(12) United States Patent  (10) Patent No.: US 8,632,553 B2
Sakamoto et al.  (45) Date of Patent: Jan. 21, 2014

(54) LIGATURE AND SUTURE DEVICE FOR MEDICAL APPLICATION, AND LIGATURING AND SUTURING METHOD FOR MEDICAL APPLICATION

(75) Inventors: Yuji Sakamoto, Tokyo (JP); Norio Onishi, Tokyo (JP); Satoshi Miyamoto, Tokyo (JP)

(73) Assignee: Olympus Corporation, Tokyo (JP)

( * ) Notice: Subject to any disclaimer, the term of this patent is extended or adjusted under 35 U.S.C. 154(b) by 1035 days.

(21) Appl. No.: 11/953,651

(22) Filed: Dec. 10, 2007

(65) Prior Publication Data

US 2008/0086153 A1  Apr. 10, 2008

Related U.S. Application Data

(63) Continuation of application No. 11/099,304, filed on Apr. 5, 2005, now Pat. No. 7,326,221.

(60) Provisional application No. 60/560,188, filed on Apr. 7, 2004.

(51) Int. Cl.
*A61B 17/10* (2006.01)

(52) U.S. Cl.
USPC .......................................................... 606/139

(58) Field of Classification Search
USPC ................................................. 606/139, 131
See application file for complete search history.

(56) References Cited

U.S. PATENT DOCUMENTS 4,557,255 A * 12/1985 Goodman ..................... 600/104
5,080,663 A  1/1992 Mills et al.

2002/0107530 A1  8/2002 Sauer et al.
2003/0120289 A1  6/2003 McGuckin, Jr. et al.
2003/0236535 A1  12/2003 Onuki et al.

FOREIGN PATENT DOCUMENTS

| JP | 2003-159254 | 6/2003 |
| JP | 2003-284722 | 10/2003 |
| JP | 2004-000601 | 1/2004 |
| JP | 2005-110983 | 4/2005 |

OTHER PUBLICATIONS

Japanese Official Action dated Sep. 14, 2010 together with a partial English language translation.

* cited by examiner

*Primary Examiner* — Gregory Anderson
(74) *Attorney, Agent, or Firm* — Scully, Scott, Murphy & Presser, P.C.

(57) ABSTRACT

A ligature and suture device for medical application includes a distal end insertion portion, a needle body, a ligature tool, and an operation section. The operation section includes a housing that is provided in a base end portion of the distal end insertion portion, a puncture handle that is provided in the housing so as to be able to move freely backwards and forwards and that drives the needle body, a pressing handle that is provided in the housing so as to be able to move freely backwards and forwards and that drives a pressing member, a ligature tool operation unit that is provided in the housing so as to be able to move freely backwards and forwards and that drives a ligature sheath, and a ligature handle that is provided in the ligature tool operation unit so as to be able to move freely backwards and forwards and that drives an engaging portion.

7 Claims, 46 Drawing Sheets

FIG.4
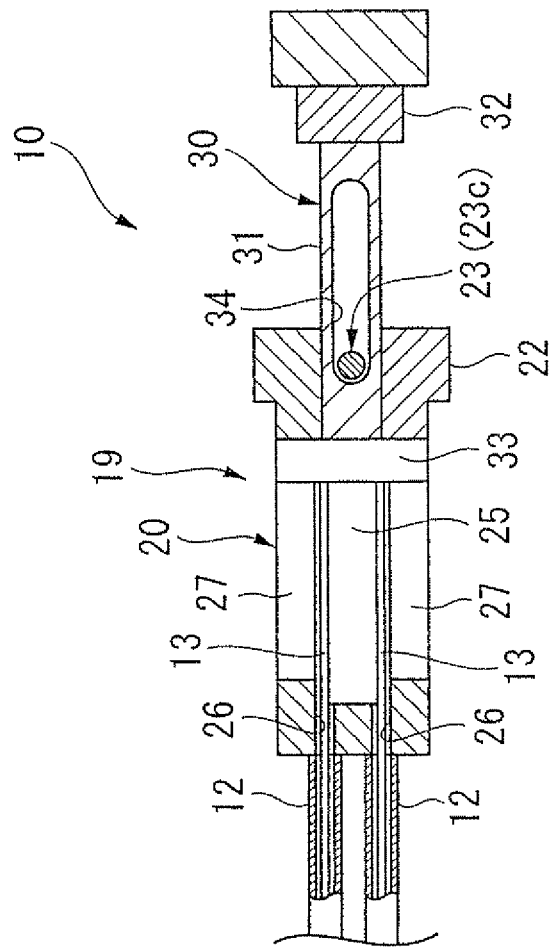
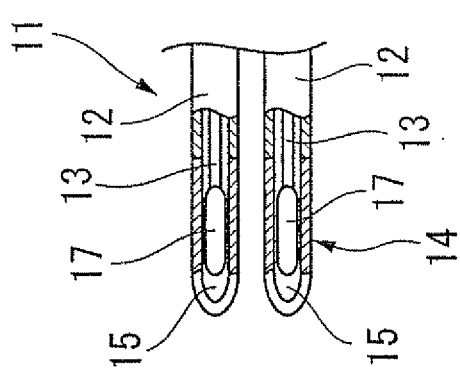

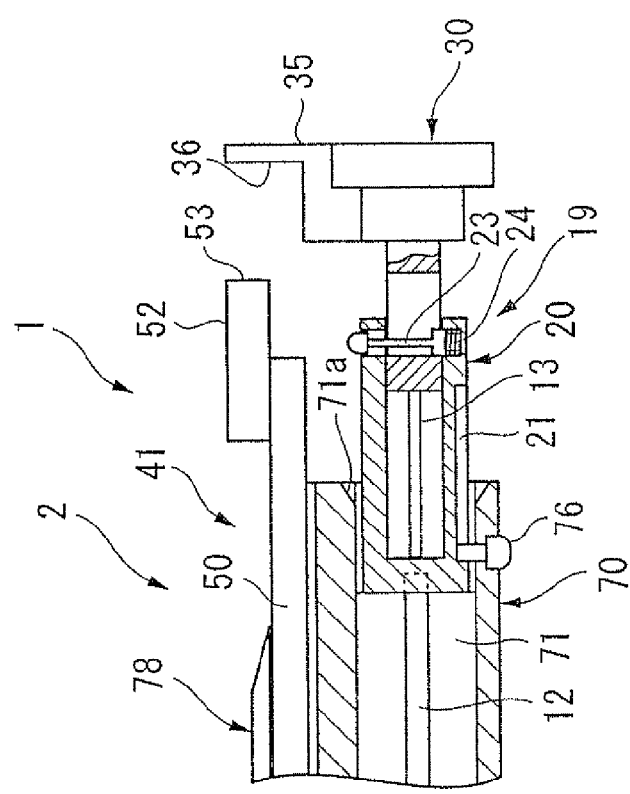
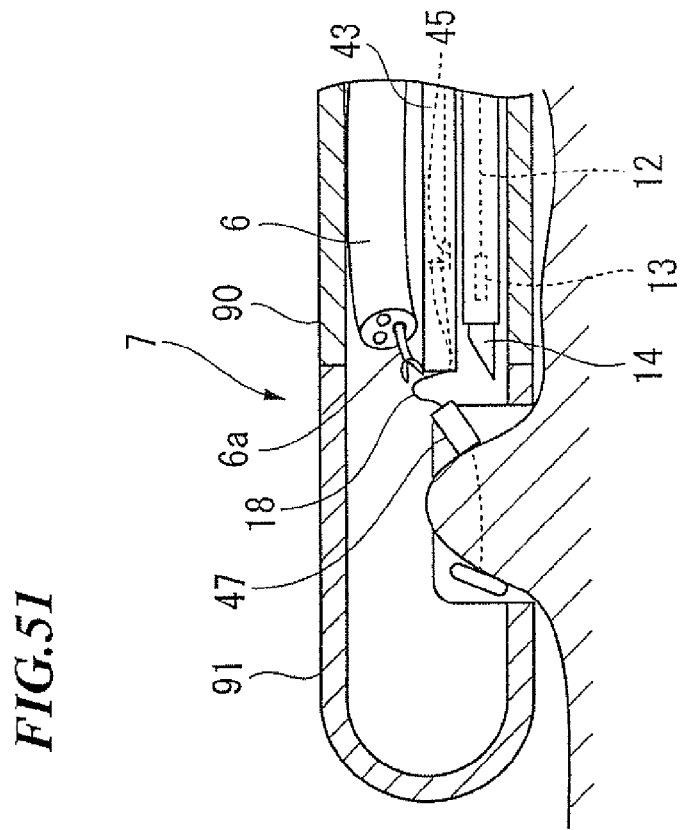
FIG.51

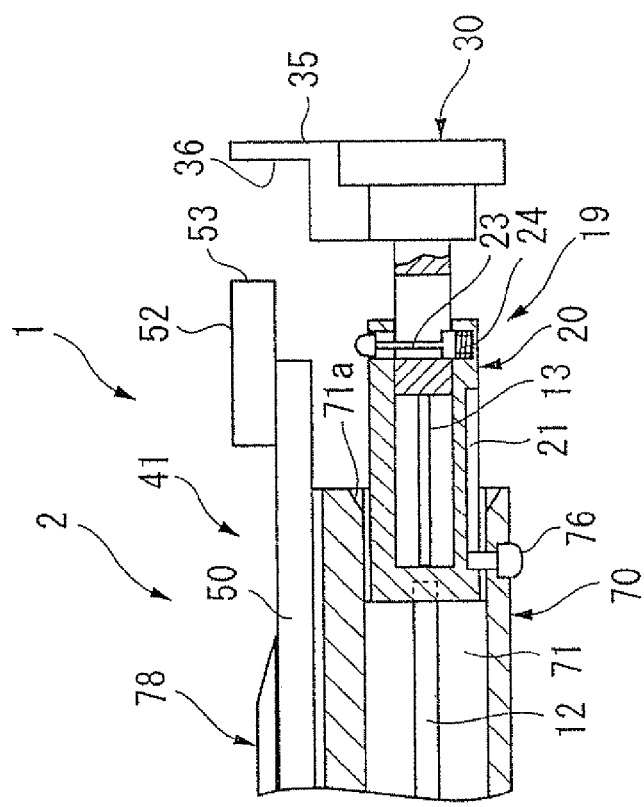
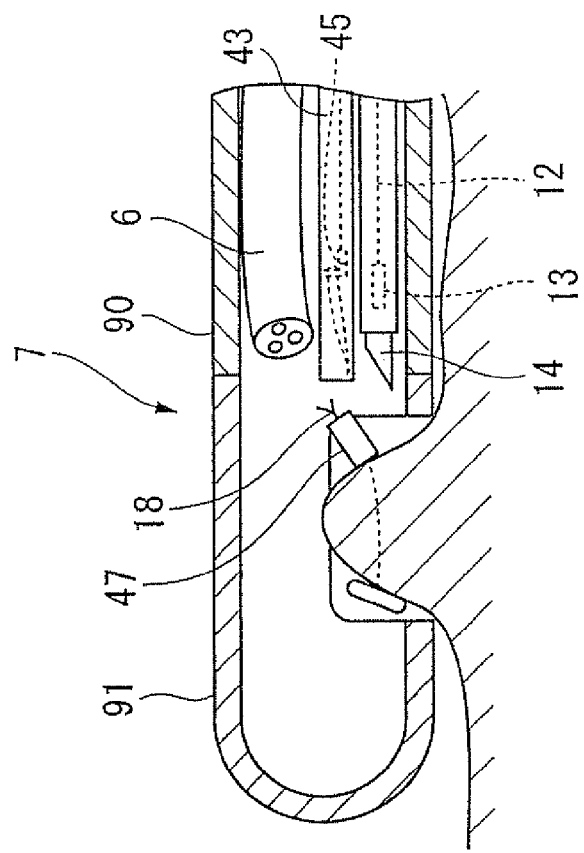
FIG.52

LIGATURE AND SUTURE DEVICE FOR MEDICAL APPLICATION, AND LIGATURING AND SUTURING METHOD FOR MEDICAL APPLICATION

CROSS REFERENCE TO RELATED APPLICATIONS

The present application is a continuation application of U.S. patent application Ser. No. 11/099,304, filed Apr. 5, 2005, which claims the benefit of U.S. Provisional Patent Application Ser. No. 60/560,188, filed Apr. 7, 2004, the contents of each of which are incorporated herein by reference.

BACKGROUND OF THE INVENTION

1. Field of the Invention

The present invention relates to a ligature and suture device for medical application that is inserted into a body and performs ligaturing or suturing or the like of biomedical tissue.

2. Description of Related Art

In recent years, the treating of biomedical tissue of a body using peroral endoscopy has increased. For example, a method of forming an artificial valve is known as a treatment for disorders such as gastroesophageal regurgitation in which the functioning of the active muscles of the lower esophagus deteriorates and gastric acid is regurgitated into the esophagus.

Here, a device exists that forms an artificial valve by ligaturing biomedical tissue so as to cause it to bulge out under observation using an endoscope (see, for example, Patent Documents 1 and 2).

In the system described in Patent Document 1, two needles for piercing the biomedical tissue are provided. A sheath that can be moved freely backwards and forwards is inserted into each needle. Furthermore, bar-shaped T-bars are fitted internally in the vicinity of the distal end of each needle. Suture thread is fixed to these T-bars. When an artificial valve is being formed using biomedical tissue, the biomedical tissue is suctioned and the resultant bulging biomedical tissue is punctured by the respective needles that point inwards from the operator side. Thereafter, the T-bars are pushed out from the needles using a pusher tube and the needles are then withdrawn. The two suture threads that penetrate the biomedical tissue are then tied, and the knot is pushed into the body using a typical knot pusher, so that the biomedical tissue on the operator side is ligatured.

Moreover, in Patent Document 2, a suture apparatus is disclosed that is provided with a needle operating section that has two needle sliders, a pusher slider, and a housing, and that is provided integrally via a base member with a grip, and with a ligature tool that is provided independently from the needle operating section.

(Patent Document 1) Japanese Unexamined Patent Application, First Publication No. 2003-159254

(Patent Document 2) US Patent Application, Publication No. 2003/0236535A1

SUMMARY OF THE INVENTION

The present invention provides a ligature and suture device for medical application, including: a distal end insertion portion that is inserted into a body cavity and in which at least one side aperture is provided; a needle body that is provided inside the distal end insertion portion, and that houses inside itself a holding member that is attached to an end portion of a ligature member that is inserted into biomedical tissue, and in which a pressing member that presses the holding member is inserted so as to be able to move freely backwards and forwards, and that is able to puncture biomedical tissue that has been made to bulge into the distal end insertion portion via the aperture; a ligature tool that has a flexible ligature sheath that presses a stopper that is penetrated by the ligature member towards the biomedical tissue, and that, at a distal end of an operating wire that has been inserted into the ligature sheath so as to be able to move freely backwards and forwards, is provided with an engaging portion that engages with the ligature member that has been inserted into the stopper; and an operation section that is provided at a base end side of the distal end insertion portion, wherein the operation section is provided with: a housing that is provided in a base end portion of the distal end insertion portion; a puncture handle that is provided in the housing so as to be able to move freely backwards and forwards and that drives the needle body; a pressing handle that is provided in the housing so as to be able to move freely backwards and forwards and that drives the pressing member; a ligature tool operation unit that is provided in the housing so as to be able to move freely backwards and forwards and that drives the ligature sheath; and a ligature handle that is provided in the ligature tool operation unit so as to be able to move freely backwards and forwards and that drives the engaging portion.

In the above ligature and suture device for medical application, the operation section may have a linking device that links the puncture handle with the pressing handle.

In the above ligature and suture device for medical application, the operation section may have a linking device that links the ligature tool operation unit with the pressing handle.

In the above ligature and suture device for medical application, the operation section may have a linking device that links the ligature tool operation unit with the puncture handle.

In the above ligature and suture device for medical application, the operation section may have a linking device that links the puncture handle with the pressing handle and the ligature tool operation unit.

The present invention further provides a ligature and suture device for medical application, including: a puncture handle that is connected via a flexible sheath to a needle body that inserts a ligature member through biomedical tissue; a pressing handle that is connected to a pressing member that is inserted into the needle body in order to press a holding member that is attached to an end portion of the ligature member; a ligature tool operation unit that is connected to a ligature sheath that presses a stopper that is penetrated by the ligature member; and a housing in which are fitted the puncture handle, the pressing handle, and the ligature tool operation unit such that each is able to move freely backwards and forwards, wherein there is also provided: a first linking device that moves the puncture handle and the pressing handle forward interconnectedly from an initial position where the puncture handle is moved back as far as possible to a tissue puncture position where the puncture handle has moved forward as far as possible and has punctured the biomedical tissue, and releases the link between the puncture handle and the pressing handle at the tissue puncture position; and a second linking device that engages the ligature tool operation unit with the pressing handle until the tissue puncture position is reached, and moves the ligature tool operation unit forward in conjunction with the pressing handle.

In the above ligature and suture device for medical application, the second linking device may push the pressing handle forward beyond the tissue puncture state, and the ligature tool operation unit may be moved forward interconnectedly with the pressing handle until the holding member is pushed out from the needle body.

In the above ligature and suture device for medical application, the second linking device may be a device that moves the pressing handle and the ligature tool operation unit forwards and backwards independently relative to the direction in which the pressing handle moves backwards.

The present invention further provides a ligaturing and suturing method for medical application in which, when biomedical tissue is ligatured using a stopper and a holding member, which are attached to a ligature member, by inserting the ligature member into the biomedical tissue by puncturing the biomedical tissue with a needle body so as to sandwich the biomedical tissue. The method includes: a step in which the needle body that houses the holding member is moved forward towards the biomedical tissue; a step in which, during the time until the needle body penetrates the biomedical tissue, the stopper is moved forward towards the biomedical tissue in conjunction with the needle body; a step in which, after the needle body has penetrated the biomedical tissue, a pressing member that is inserted in the needle body is moved forward so as to push out the holding member that is housed in the needle body; and a step in which, after the needle body has been withdrawn from the biomedical tissue, the ligature member that is inserted in the stopper is pulled so that the biomedical tissue is sandwiched by the stopper and the holding member and is ligatured.

In the above ligature and suture method for medical application, there may be provided a step in which, after the needle body has punctured the biomedical tissue, the stopper is moved forward in conjunction with the forward movement of the pressing member.

In the above ligature and suture method for medical application, there may be provided a step in which, when the needle body is being removed from the biomedical tissue, the needle body is moved backward in conjunction with the backward movement of the pressing member.

In the above ligature and suture method for medical application, when the needle body is being removed from the biomedical tissue, the needle body may be moved backwards independently from the stopper.

BRIEF DESCRIPTION OF THE DRAWINGS

FIG. 4 is a cross-sectional view taken along a line IV-IV in FIG. 3.

FIG. 51 is a view showing the layout when the ligature thread is cut by forceps of an endoscope in another embodiment of the present invention.

FIG. 52 is a view showing a state in which the ligature thread is cut by the forceps of the endoscope.

DETAILED DESCRIPTION OF THE INVENTION

Embodiments for implementing the present invention will now be described in detail with reference made to the drawings.

(First Embodiment)

Figure 1:
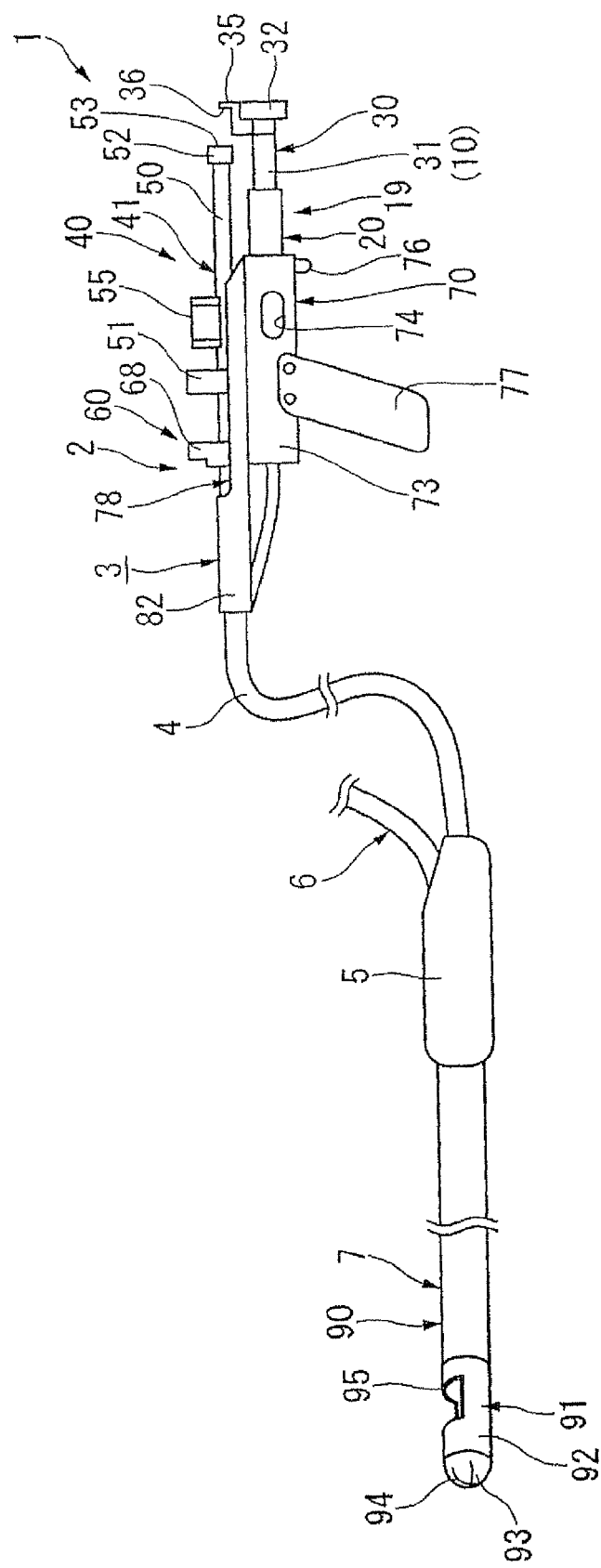
FIG. 1 is a schematic view showing the structure of a ligature and suture device for medical application according to a first embodiment of the present invention.
Figure 2:
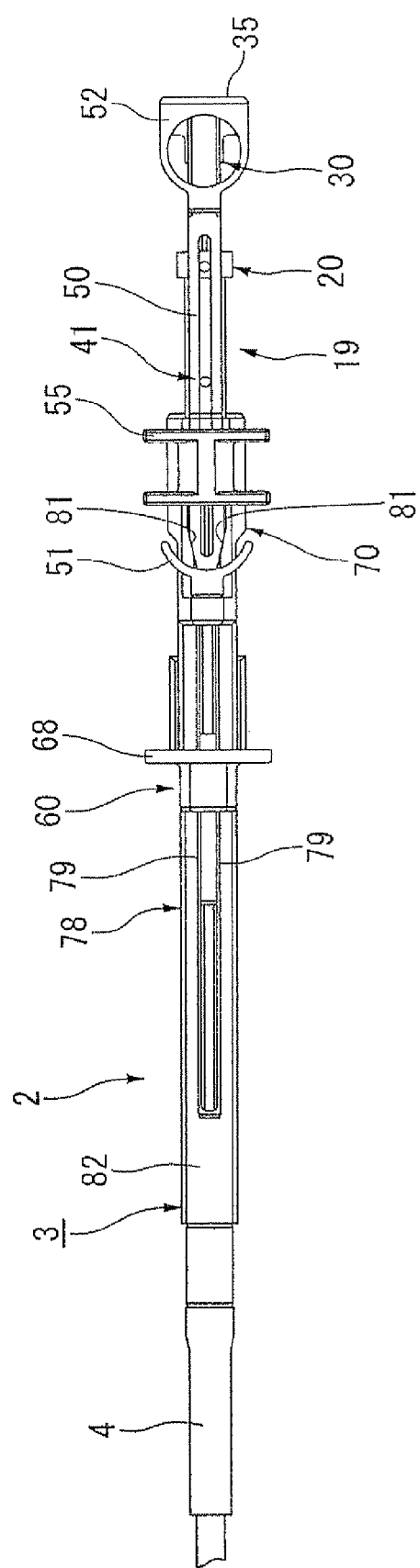
FIG. 2 is a top view of an operation section side of a ligature and suture device for medical application.

A first embodiment of the present invention will be described with reference to FIGS. 1 to 29. As shown in FIGS. 1 and 2, a ligature and suture apparatus for medical application 1 according to the present embodiment is provided with an operating section 2 that is operated by a doctor, and a flexible tube 4 is mounted on the distal end of a housing 3 of this operating section 2. An endoscope insertion portion 5 is fixed to a distal end of the tube 4, and an endoscope 6 is inserted from here. A flexible overtube 7, which is a distal end insertion portion that is inserted into a body cavity, is mounted on a distal end of the endoscope insertion portion 5. In addition, an insertion portion 11 of a treatment tool in the form of a puncture needle 10, such as that shown in FIG. 3 and FIG. 4, and an insertion portion 42 of a ligature tool 40, such as that shown in FIG. 6, are inserted from the housing 3 side into the overtube 7.

Figure 3:
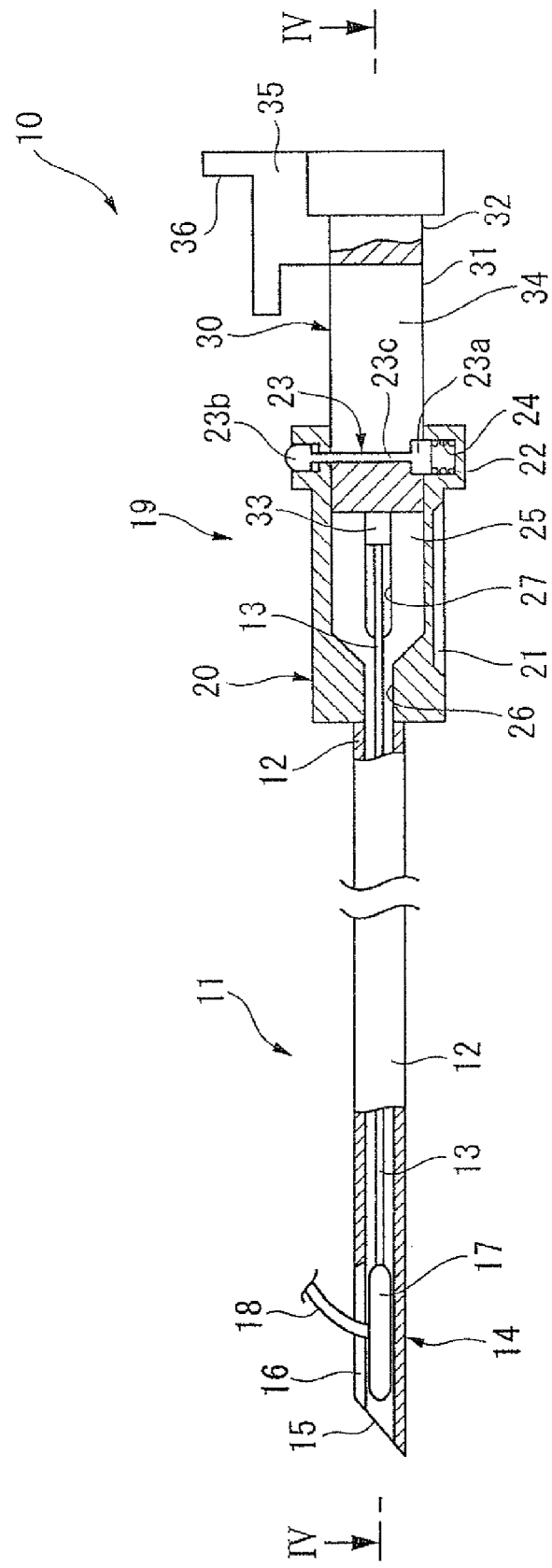
FIG. 3 is a cross-sectional view showing the structure of a puncture needle.

As shown in FIG. 3 and FIG. 4, the insertion portion 11 of the puncture needle 10 has a flexible inner sheath 12, and a pushing member in the form of a pusher 13 that is inserted so as to be able to move freely backwards and forwards inside the inner sheath 12. A needle body 14 is fixed to a distal end of the inner sheath 12. The needle body 14 has a circular cylinder configuration, and a distal end aperture portion 15 thereof is cut so as to be diagonally inclined. As shown in FIG. 3, a slit 16 is provided extending in the longitudinal direction from a peripheral portion of the distal end aperture portion 15. Note that a holding member 17 is housed in the needle body 14. The holding member 17 is attached to an end portion of a ligature thread (i.e., a ligature member) 18, and is known as a T-bar. The ligature thread 18 is pulled to the outside of the needle body 14 via the slit 16. The pusher 13 is inserted into the inner sheath 12 in order to push the holding member 17 and the ligature thread 18 out from inside the needle body 14. Note that the puncture needle 10 is provided with two inner sheaths 12 and two needle bodies 14 arranged in parallel with each other.

This insertion portion 11, which is provided with two pushers 13 and two inner sheaths 12, is connected to a puncture needle operation unit 19 for the puncture needle 10. The puncture needle operation unit 19 has a puncture handle 20 to which the inner sheaths 12 are fixed. The puncture handle 20 has a substantially circular cylinder configuration, and, as shown in FIG. 3, a groove 21 is formed on an outer circumferential surface thereof extending in the longitudinal direction thereof from a distal end portion of the puncture handle 20 to a base end portion thereof. Furthermore, the base end portion of the puncture handle 20 is formed so as to be enlarged on the outer side in the radial direction, such that it can be easily gripped by a doctor. A linking pin 23, which forms a first linking device, is inserted into this enlarged diameter portion 22. The linking pin 23 passes through the center of the enlarged diameter portion 22, and a base portion 23a thereof is urged to the upper side (i.e., upwards) as seen in FIG. 3 by an elastic member 24 such as a coil spring. A distal end portion 23b of the linking pin 23 protrudes partially from the enlarged diameter portion 22. An intermediate portion 23c is formed between the base portion 23a and the distal end portion 23b of the linking pin 23, and the diameter of the intermediate portion 23c is smaller than that of the base portion 23a.

Furthermore, a slide hole 25 is provided in the puncture handle 20 extending from the base end surface thereof towards the distal end portion. The slide hole 25 communicates with two through holes 26 that are provided in the distal end portion of the puncture handle 20. The two through holes 26 are provided in parallel with each other, and the diameters of each of these are large enough so that the two pushers 13 can each be inserted therein and moved freely backwards and forwards. In addition, slits 27 are provided in parallel with the longitudinal direction of the puncture handle 20 in an outer portion of the puncture handle 20 so as to be connected to the slide hole 25. Two of these slits 27 are provided at positions whose phases are 180 degrees apart from each other. Note that the two slits 27 are provided along a plane that is orthogonal to the linking pin 23.

A pressing handle 30 is inserted into the slide hole 25 of the puncture handle 20 so as to be able to move backwards and forwards. The pressing handle 30 has a slide portion 31, which has a substantially columnar configuration, and a handle body 32 is fixed to a base end of the slide portion 31.

The slide portion 31 has an outer diameter that enables it to slide freely inside the slide hole 25, and a guide member 33 is fixed to a distal end of the slide portion 31. The guide member 33 slides inside the slits 27 of the puncture handle 20, and the two pushers 13 are fixed in parallel with each other to the distal end of the guide member 33. Furthermore, a slit 34 is provided in the slide portion 31 in parallel with the longitudinal direction thereof. The slit 34 penetrates the slide portion 31 vertically, and the intermediate portion 23c of the linking pin 23 is inserted into the slit 34. The width of the slit 34 is narrower than that of the base portion 23a of the linking pin 23. However, a notch is made in a bottom side of the distal end portion of the slit 34 so that a portion thereof can be engaged with the base portion 23a of the linking pin 23.

The handle body 32 has a larger diameter than that of the slide portion 31, and a linking member 35 is fixed to top portion of the handle body 32. A contact surface 36 is provided in the linking member 35 (which forms a second connecting device) that makes contact with a finger piece portion 52 of the ligature tool 40 (described below) so as to engage with the finger piece portion 52.

Figure 5:
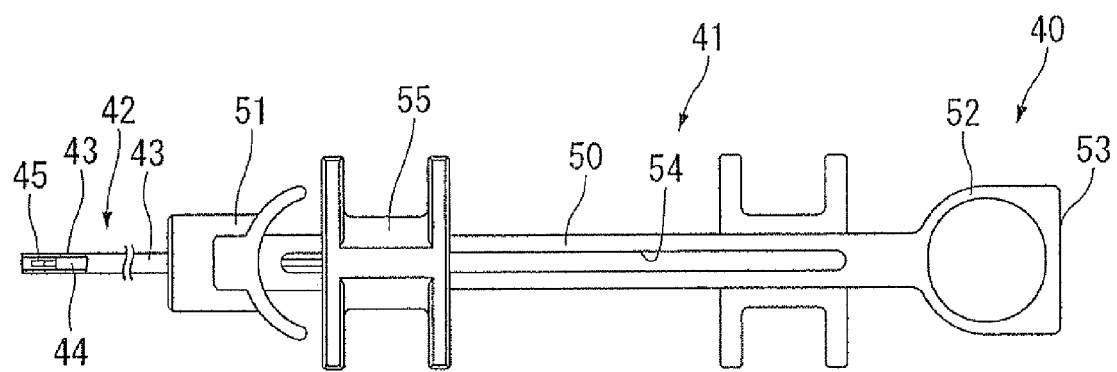
FIG. 5 is a top view showing the structure of a ligature tool.
Figure 6:
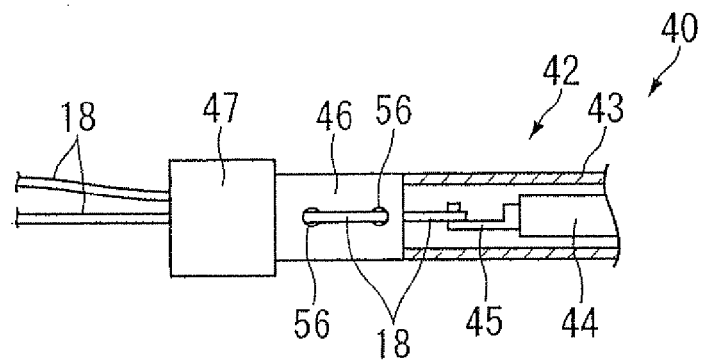
FIG. 6 is a partial cross-sectional view showing a distal end portion of the ligature tool.

As shown in FIG. 5, the ligature tool 40 has a ligature tool operation unit 41 (a ligature portion), and a flexible insertion portion 42 is provided in a distal end of the ligature tool operation unit 41. In the insertion portion 42, an operating wire 44 is inserted inside the ligature sheath 43 so as to be able to move freely backwards and forwards. An engaging portion in the form of a hook 45 that can be engaged with the ligature thread 18 is attached to a distal end of the operating wire 44. As shown in FIG. 6, a stopper 47 is placed at a distal end of the ligature sheath 43 sandwiching a cutter receiving portion 46.

As shown in FIG. 5, the ligature tool operation unit 41 has a substantially columnar shaped main body portion 50. A base end of the ligature sheath 43 is fixed to a distal end portion of the main body portion 50. Furthermore, a knob portion 51 is fixed to the distal end portion of the main body portion 50. The knob portion 51 is the portion that is gripped by a doctor when the doctor operates a ligature handle 55 (described below). The finger piece portion 52 is attached to a base end of the main body portion 50. A base end of this finger piece portion 52 forms a flat surface 53, and this flat surface 53 comes into contact with the contact surface 36 of the linking member 35. Furthermore, a slit 54 is provided in the main body portion 50 in parallel with the longitudinal direction of the main body portion 50. The slit 54 vertically penetrates the main body portion 50, and the ligature handle 55 is attached here so as to be able to slide freely. The base end portion of the operating wire 44, which is inserted into the main body portion 50 so as to be able to move freely backwards and forwards, is fixed to the ligature handle 55.

The cutter receiving portion 46 shown in FIG. 6 is a circular cylindrical member whose base end portion is in contact with the ligature sheath 43. Through holes 56 are provided in a side wall portion of the cutter receiving portion 46. Two through holes 56 are arranged in the longitudinal direction of the cutter receiving portion 46 as seen in side view, and two through holes are also provided in the same manner at positions whose phases are 180 degrees apart to give a total of four through holes 56. The ligature thread 18 that has been pulled out through the stopper 47 is inserted into the cutter receiving portion 46. The ligature thread 18 is inserted from inside an aperture in the distal end portion of the cutter receiving portion 46 and runs through the through holes 56 on the distal end side towards the outside. After passing along the outer circumferential surface of the cutter receiving portion 46, the ligature thread 18 is inserted through the through holes 56 on the base end side running towards the inside, and is introduced into the ligature sheath 43 from an aperture on the base end side.

The stopper 47 is manufactured from silicon resin or the like, and an intermediate portion of the ligature thread 18, both end portions of which are attached to the holding member 17, is inserted into the stopper 47. The stopper 47 uses friction to engage with the ligature thread 18, and is used to ligature biomedical tissue together with the holding member 17 (see FIG. 3).

Figure 7:
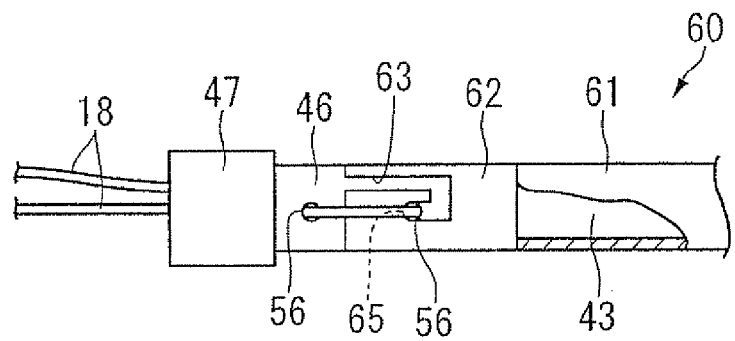
FIG. 7 is a view showing the layout of the distal end portion of the ligature tool and a cutter portion.

Here, as shown in FIG. 1 and FIG. 7, in the present embodiment, a cutter 60 that cuts the ligature thread 18 inside a body cavity is externally mounted on the ligature tool 40. The cutter 60 has a flexible cutter sheath 61 that covers an outer circumference of the ligature sheath 43 such that the ligature sheath 43 can move freely backwards and forwards. The position of the distal end of the cutter sheath 61 matches the position of the distal end of the ligature sheath 43. A cutter portion 62 is fixed to the distal end of this cutter sheath 61.

Figure 8:
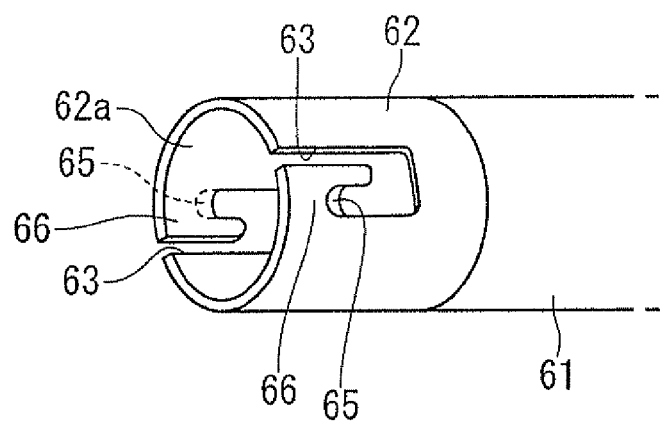
FIG. 8 is a prospective view showing the layout of the cutter portion.

The cutter portion 62 covers an outer circumferential surface of the base end side of the cutter receiving portion 46, and the inner diameter of the cutter portion 62 is substantially equal to the outer diameter of the cutter receiving portion 46. As shown in FIG. 8, two notches 63 are provided at positions whose phases are 180 degrees apart in the cutter portion 62. Each notch 63 has a base end at an aperture 62a of the distal end portion. Each notch 63 extends from there in the longitudinal direction of the cutter portion 63, and turns in a circumferential direction in the vicinity of substantially the middle in this longitudinal direction. The notches 63 then extend in this circumferential direction, and then turn back towards an edge portion of the aperture 62a. A blade portion 65 is formed at this turning back end portion. As shown in FIG. 7, in an initial state, the cutter portion 62 is placed at a position where the end portion of the notches 63 connect to the through holes 56 on the base end side of the cutter receiving portion 46. Of that portion of the ligature thread 18 that is inserted into the cutter portion 46, the portion thereof that passes along the outer circumferential surface of the cutter receiving portion 46 is guided around so as to catch on a shoulder portion 66 that is formed by the notches 63. Namely, the ligature thread 18 is pulled out from the through holes 56 on the distal end side of the cutter receiving portion 46, passes along the outer circumferential surface of the shoulder portion 66 of the cutter portion 62, passes through the through holes 56 from the end portions of the notches 63, and is inserted into the cutter receiving portion 46.

In addition, as shown in FIG. 1, the base end of the cutter sheath 61 is fixed to a cutter handle 68 that is attached to a top portion (i.e., on the upper side in FIG. 1) of the housing 3 so as to be able to move freely backwards and forwards.

Next, a description will be given of the housing 3 in which the puncture needle operation unit 19 and the ligature tool operation unit 41 are installed.

Figure 9:
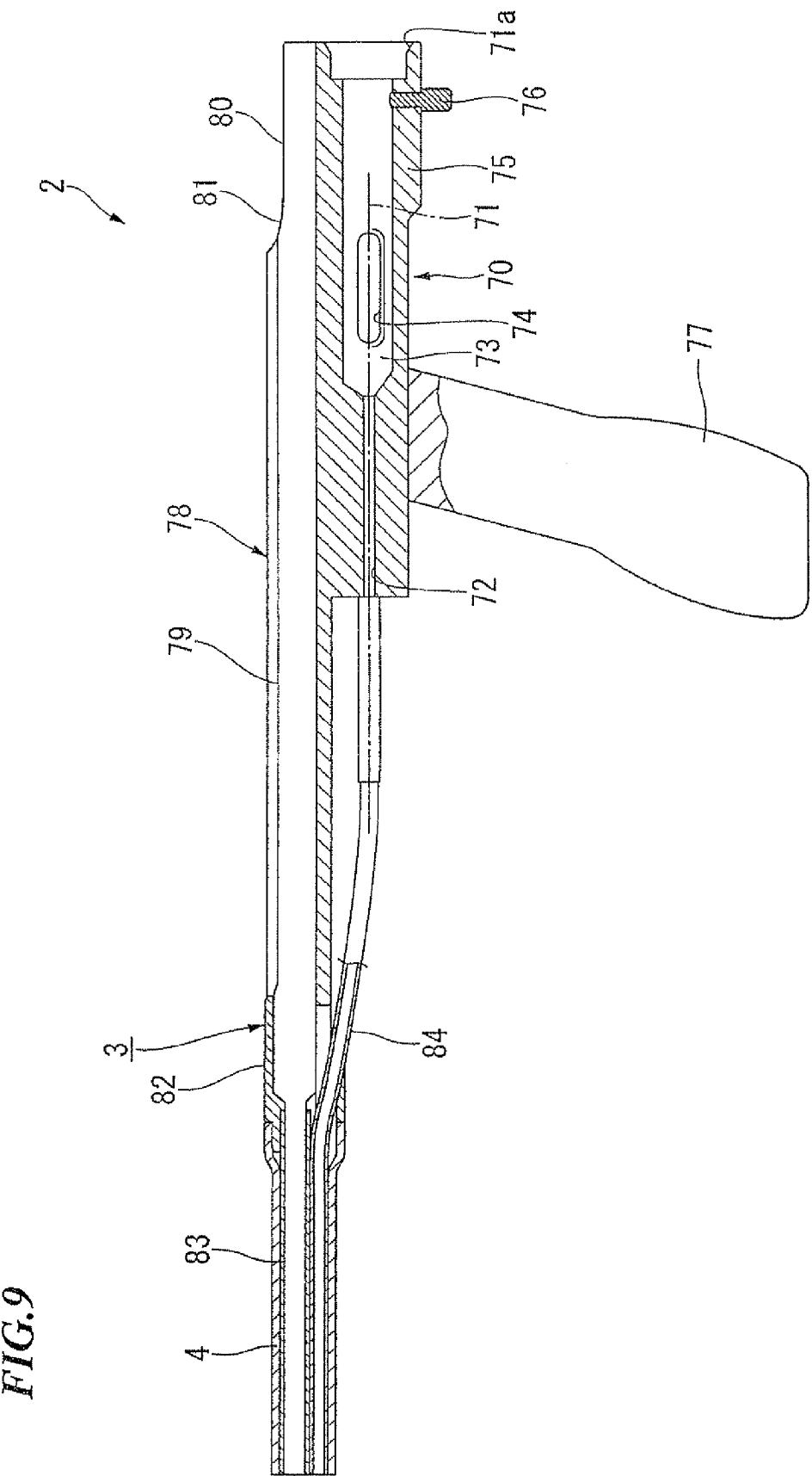
FIG. 9 is a side cross-sectional view showing the structure of a housing.

As shown in FIG. 9, a housing portion 70 into which the puncture needle operation unit 19 can be inserted so as to be able to move freely backwards and forwards is provided on a base end side of and below the housing 3. The housing portion 70 is formed substantially as a rectangular parallelepiped, and a substantially columnar insertion hole 71 is formed in the interior thereof. A tapered surface 71a is formed at a base end portion of the insertion hole 71 so as to increase the diameter thereof. The puncture handle 20 (see FIG. 3) is inserted into the insertion hole 71. Through holes 72 that connect the insertion hole 71 with the distal end surface of the housing portion 70 are formed in the distal end portion of the housing portion 70. Two through holes 72 are formed in parallel, and an inner sheath 12 is inserted in each through hole 72 so as to be able to move freely backwards and forwards. Lighting windows 74 are formed in each side wall portion 73 of the housing portion 70. An engaging screw 76 screws into a base end side of a bottom portion 75 of the housing portion 70. Furthermore, a grip 77 is attached to the bottom portion 75 of the housing portion 70. The grip 77 extends diagonally forwards (i.e., towards the distal end side and also the lower side of the housing 3) from the housing portion 70.

Figure 10:
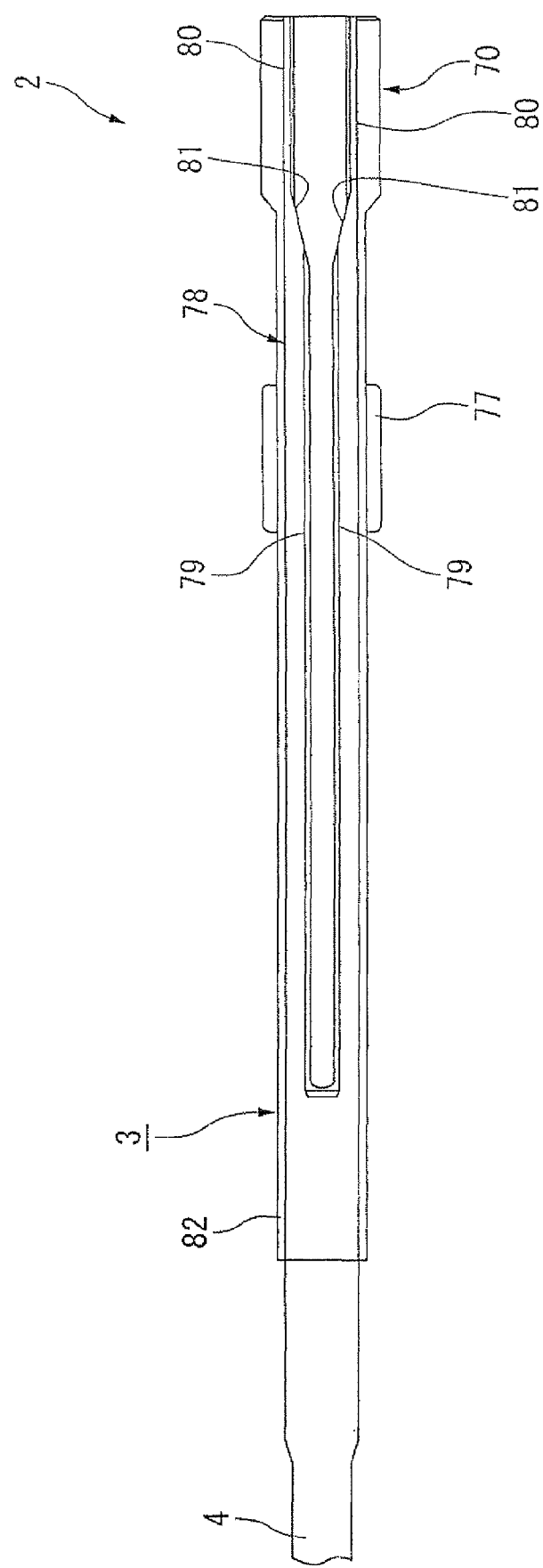
FIG. 10 is a top view of the housing.

A slide receiving portion 78 is provided above the housing portion 70 in the housing 3. The slide receiving portion 78 extends towards the distal end side beyond the housing portion 70. As shown in FIG. 9 and FIG. 10, the slide receiving portion 78 is formed having a substantially C shaped cross-section so that a top portion thereof forms open ends 79. In addition, a notch is cut in the vicinity of the open ends 79 in a base end side of the slide receiving portion 78. As a result of this notch 80, colliding portions 81 are formed in which the distance between the open ends 79 gradually increases.

As shown in FIG. 9, a housing distal end portion 82 is provided at a distal end of the slide receiving portion 78. An outer sheath 83 and two outer sheaths 84 that are arranged in parallel with each other are inserted into the housing distal end portion 82. The outer sheath 83 is fixed to the housing distal end portion 82 such that an aperture at a base end of the outer sheath 83 is continuous with the slide receiving portion 78. The two outer sheaths 84 are drawn out below the housing distal end portion 82, and are each fixed so as to cover the respective through holes 72 of the housing portion 70.

Figure 11:
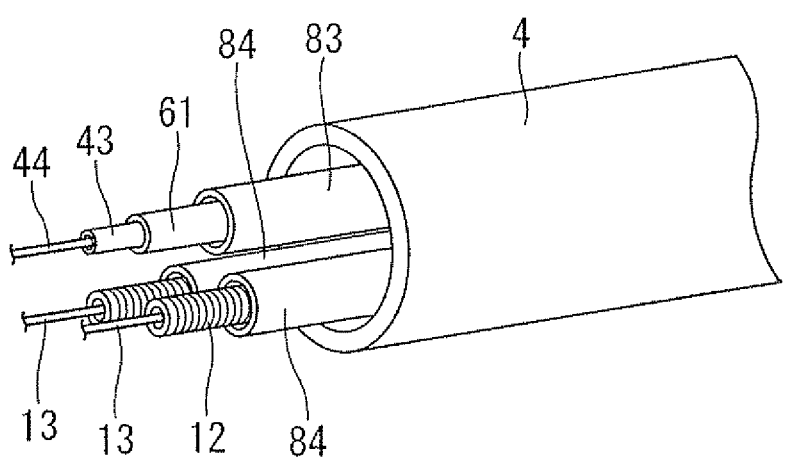
FIG. 11 is a perspective view showing the cross-section of a tube.

As shown in FIG. 11, each of the outer sheaths 83 and 84 is inserted into a tube 4 that is fixed to the distal end of the housing 3, and is guided into the overtube 7 shown in FIG. 1. The overtube 7 has a substantially circular cylinder shaped tube main body 90 and a distal end tube 91 that can be freely attached to and removed from a distal end of the tube main body 90. A distal end of the circular cylinder portion of the distal end tube 91 is closed off in a dome shape to form a dome portion 93. Slits 94 are provided in the dome portion 93, so that the dome portion 93 is split into a plurality of valve elements. An elongated hole is formed running in the circumferential direction in a circular cylinder portion 92, and this elongated hole forms a side aperture and 95 where biomedical tissue is suctioned.

Figure 12A:
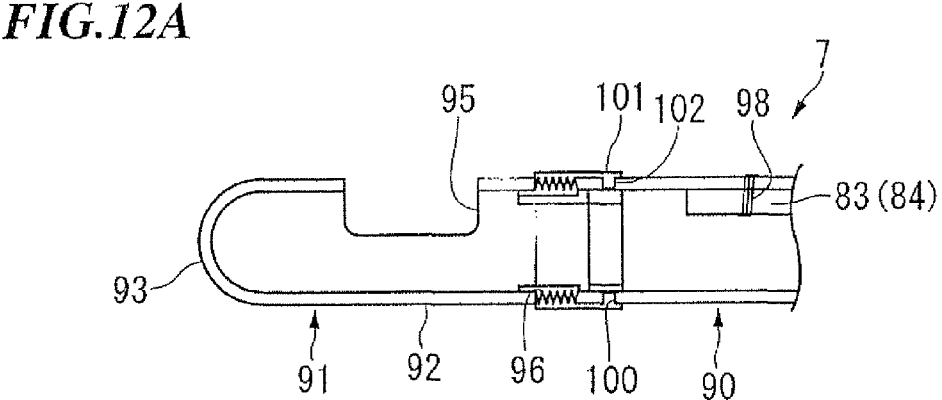
FIG. 12A is a cross-sectional view showing an overtube in a state in which a distal end tube is connected to a tube main body.
Figure 12B:
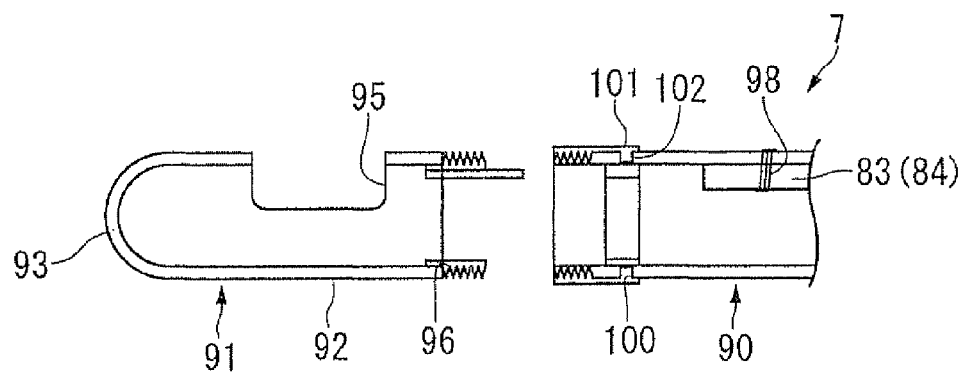
FIG. 12B is a cross-sectional view showing the overtube in a state in which the distal end tube is separated from the tube main body.
Figure 13:
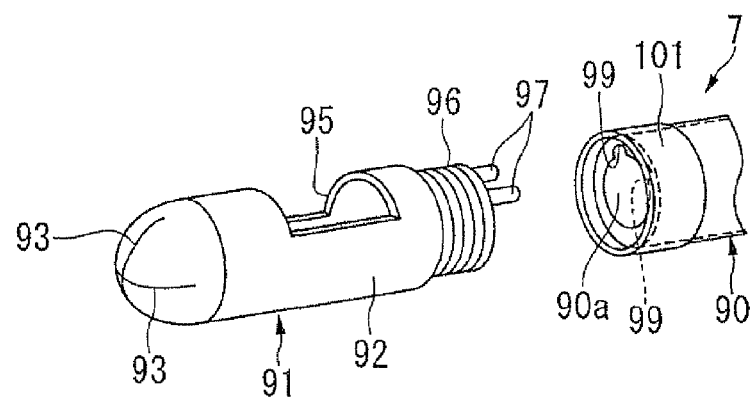
FIG. 13 is a perspective view showing a state in which the distal end tube is separated from the tube main body.

As shown in FIGS. 12A, 12B, and 13, an engaging portion 96 is provided at a base end of the circular cylinder portion 92. In the engaging portion 96, a thread is cut in an outer circumferential surface of a toroidal member. In addition, as shown in FIG. 13, two positioning pins 97 extend in parallel with the axial direction from the engaging portion 96.

Distal end portions of each of the outer sheaths 83 and 84 are tightly bound using thread 98 to an inner wall of the tube main body 90 on the base end side thereof at a predetermined distance from a distal end aperture 90a of the tube main body 90. The position of the distal end portions of each of the sheaths 83 and 84 is a position where an operation of the puncture needle 10 and ligature tool 40 (described below) is not obstructed, and the thread 98 is used as a fixing device because it is difficult to apply an adhesive agent coating at a position such as this.

A receiving portion 99 that engages with the pins 97 is provided in a concave configuration in the distal end aperture 90a of the tube main body 90. Furthermore, a toroidal groove 100 is formed in an outer circumference in the vicinity of the distal end aperture 90a, and a toroidal projection 102 of a toroidal ring of 101 fits here into the groove 100. The rotating ring 101 is rotatably attached so as to cover the outer circumference of the tube main body 90. A distal end portion of the rotating ring 101 protrudes beyond the tube main body 90, and a thread is cut into an inner circumferential surface of this protruding portion. This thread is able to be engaged with the thread on the engaging portion 96 on the distal end tube 91 side.

An operation of the present embodiment will now be described.

Figure 14:
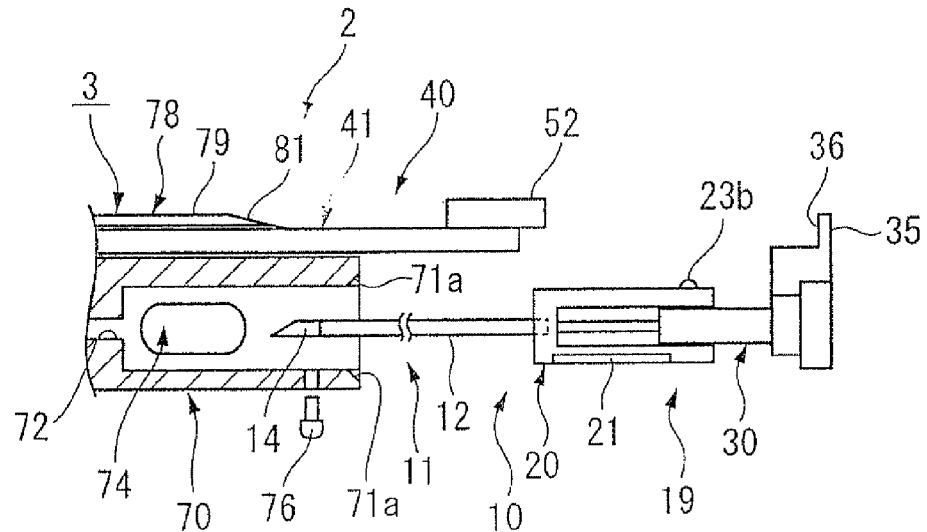
FIG. 14 is a view for showing an operation when a puncture needle is inserted.
Figure 15:
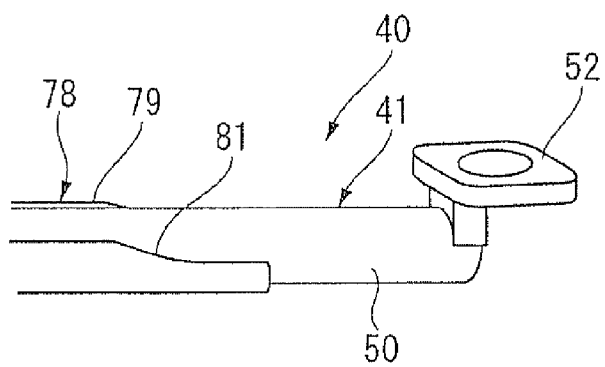
FIG. 15 is a perspective view showing a position in an initial state of the ligature tool.
Figure 16:
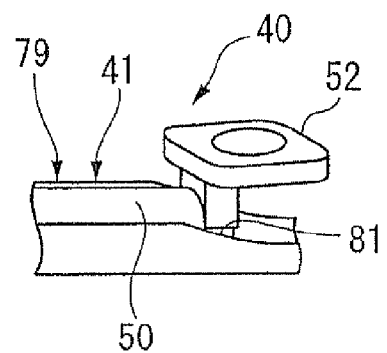
FIG. 16 is a perspective view showing a state in which the ligature tool is moved further forward.

As shown in FIG. 14, in order to attach the puncture needle 10, each of the needle bodies 14 is inserted respectively into the two through holes 72 of the housing portion 70 of the housing 3. The needle bodies 14 are positioned in the through holes 72 using light that is guided into the housing portion 70 from the lighting window 74 that is formed in the side wall portion 73.

Once the needle bodies 14 have been inserted into the housing portion 70, the inner sheaths 12 are moved forward so that the respective needle bodies 14 and inner sheaths 12 are moved from the housing portion 70 into the respective outer sheaths 84. The puncture needle operation unit 19 is also inserted into the housing portion 70. At this time, the puncture needle operation unit 19 is inserted such that the groove 21 in the puncture handle 20 matches the threaded hole of the engaging screw 76 of the housing portion 70. Once the puncture needle operation unit 19 has been inserted, the engaging screw 76 is screwed in so that the distal end thereof is made to protrude into the groove 21. As a result, the puncture handle 20 is able to move forwards or backwoods relative to the housing 3 between the base end and the distal end of the groove 21, while at the same time the removal of the puncture handle 20 is prevented. At this time, the two needle bodies 14 protrude from the outer sheaths 84 inside the overtube 7 (see FIG. 1), and are placed in a first position in the vicinity of the side aperture 95.

When fitting the ligature tool 40, after the insertion portion 42 has been inserted into the cutter sheath 61, the entire cutter sheath 61 is inserted into the outer sheath 83. Furthermore, the cutter handle 68 and the main body portion 50 of the ligature tool operation unit 41 are inserted into the slide receiving portion 78 of the housing 3. The ligature tool 40 is able to be moved forwards and backwards from an initial position shown in FIG. 2 and FIG. 15 to an advance position such as that shown in FIG. 16. This advance position is a position where the colliding portion 81 comes into contact with the finger piece portion 52.

Figure 17:
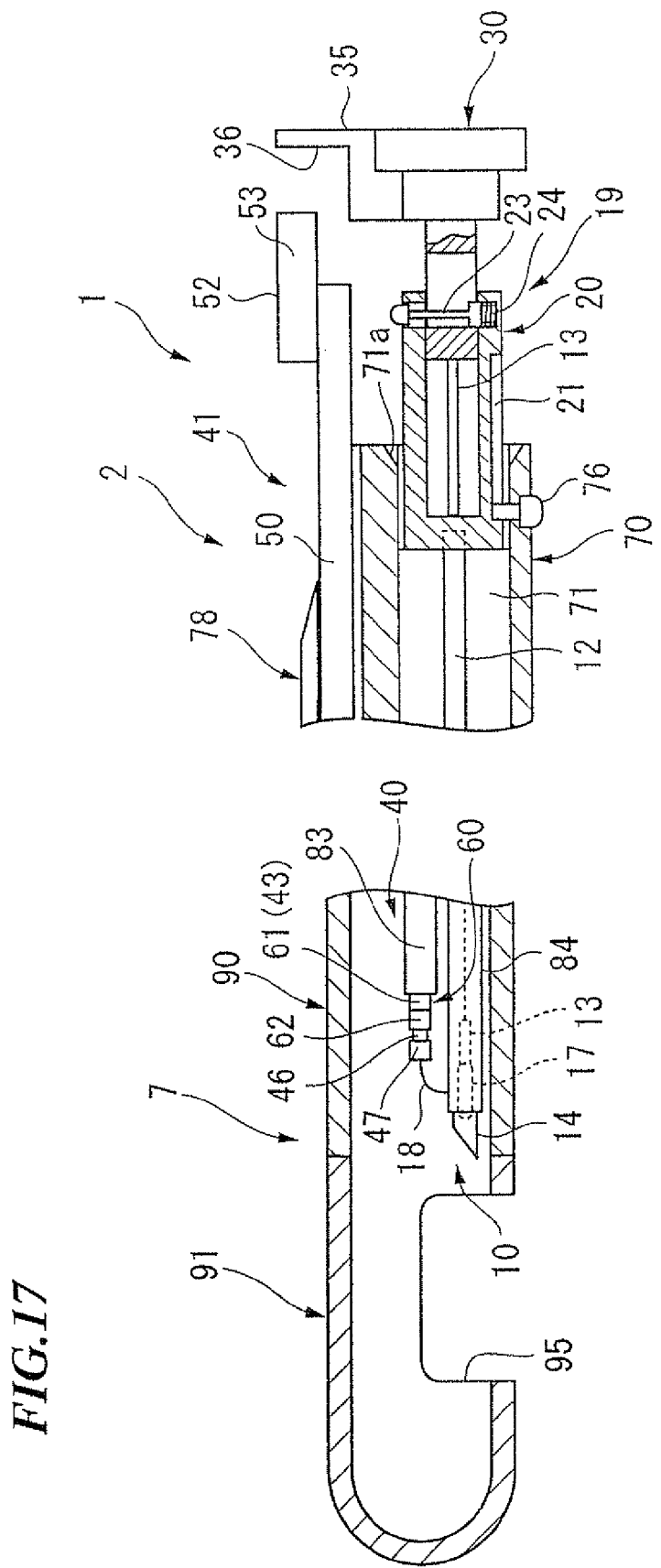
FIG. 17 is a view showing the operation of a ligature and suture device for medical application, and is a view showing the layout in an initial state.

Note that, as shown in FIG. 17, if the puncture needle 10 and ligature tool 40 as well as the cutter 60 are installed, the positions of each portion at this time become the initial positions (corresponding to the first position). The distal end of the insertion portion 42 is placed inside the overtube 7 a predetermined distance on the base end side beyond the respective needle bodies 14.

When the two holding members 17, to which are attached the ligature threads 18, are fitted to each of the needle bodies 14, as shown in FIG. 13, the distal end tube 91 of the overtube 7 is removed. At this time, the distal end tube 91 and the tube main body 90 are held while the rotating ring 101 is rotated. Once the distal end tube 91 has been removed, the holding members 17 are each inserted via the apertures in each needle body 14, and the ligature threads 18 are drawn out from the slits 16 (see FIG. 3) in the needle bodies 14.

Furthermore, as shown in FIG. 6, when fitting the stopper 47 and the cutter receiving portion 46 in the ligature tool 40, the ligature handle 55 shown in FIG. 5 is made to advance towards the distal end side so that the hook 45 is exposed from the ligature sheath 43. As shown in FIG. 6, the ligature thread 18, which has been formed into a loop by the stopper 47 and the cutter receiving portion 46, is then hooked onto the hook 45, and the manipulation of the ligature handle 55 is ended. Because a spring (not shown) has been inserted between the ligature handle 55 and the knob portion 51, the ligature handle 55 automatically returns to its initial position, and the hook 45 together with the ligature thread 18 that is hooked onto the hook 45 are pulled inside the ligature sheath 43. As a result, the cutter receiving portion 46 and the stopper 47 are held in this sequence at the distal end of the ligature sheath 43.

Figure 18:
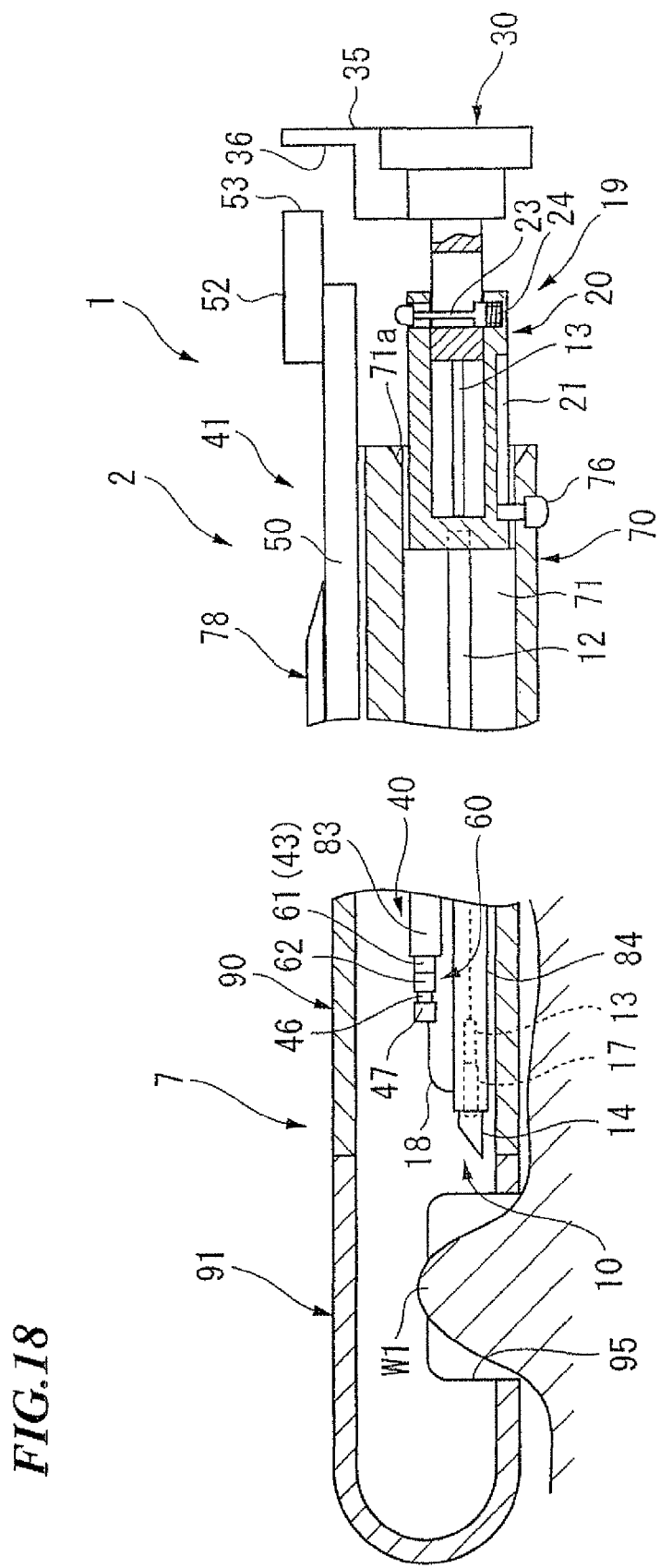
FIG. 18 is a view showing the operation when a pressing handle is moved forward.

When ligaturing biomedical tissue, the endoscope 6 is inserted from the endoscope insertion portion 5 shown in FIG. 1, and the overtube 7 is inserted into a body cavity. When the side aperture 95 of the overtube 7 has arrived at the position of the ligature object (i.e., at the target position), a suction device (not shown) of the endoscope 6 is operated, and the target position is suctioned inside the overtube 7 via the side aperture 95. As a result, as shown in FIG. 18, biomedical tissue W1 is suctioned inside the overtube 7.

Once the biomedical tissue W1 has been suctioned, an operator pushes in the pressing handle 30 towards the distal end side so as to make the respective needle bodies 14 advance towards the biomedical tissue W1. At this time because the pressing handle 30 and the puncture handle 20 are linked by the linking pin 23, the puncture handle 20 moves forward in conjunction with the pressing handle 30, so that, as a result, each inner sheath 12 and each pusher 13 moves forward simultaneously. Note that, in FIG. 18, because the ligature tool 40 is not operated, the stopper 46 is not moved forward.

Figure 19:
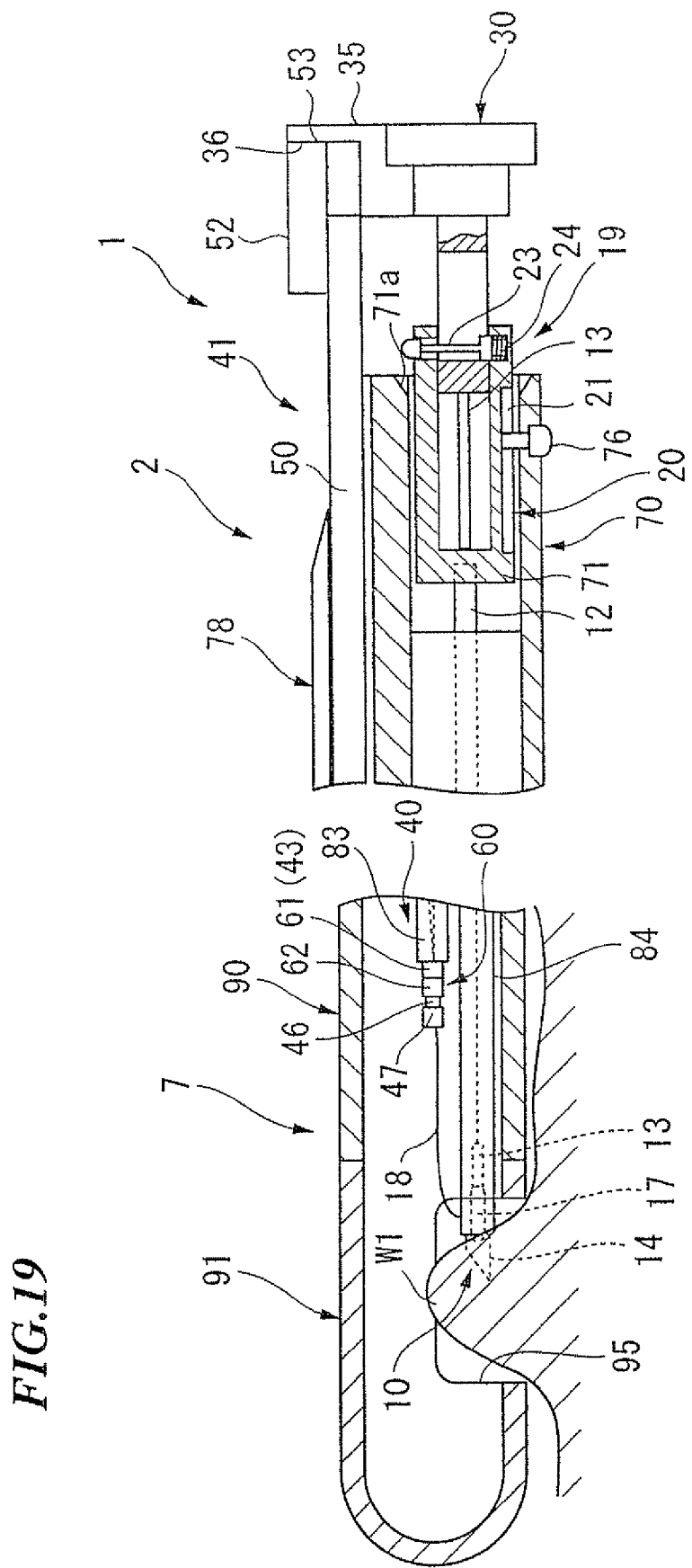
FIG. 19 is a view showing a state in which the pressing handle and the ligature tool move together.

If the pressing handle 30 is pushed in further, then as shown in FIG. 19, the linking member 35 of the pressing handle 30 comes into contact with the finger piece portion 52 of the ligature tool operation unit 41 and engages therewith. As a result, the pressing handle 30 is engaged with the ligature tool operation unit 41, so that if the pressing handle 30 is made to move forward, the ligature tool 40 and the puncture handle 20 also move forward in conjunction with the pressing handle 30 and the distance between the holding member 17 and the stopper 47 is kept substantially constant.

Figure 20:
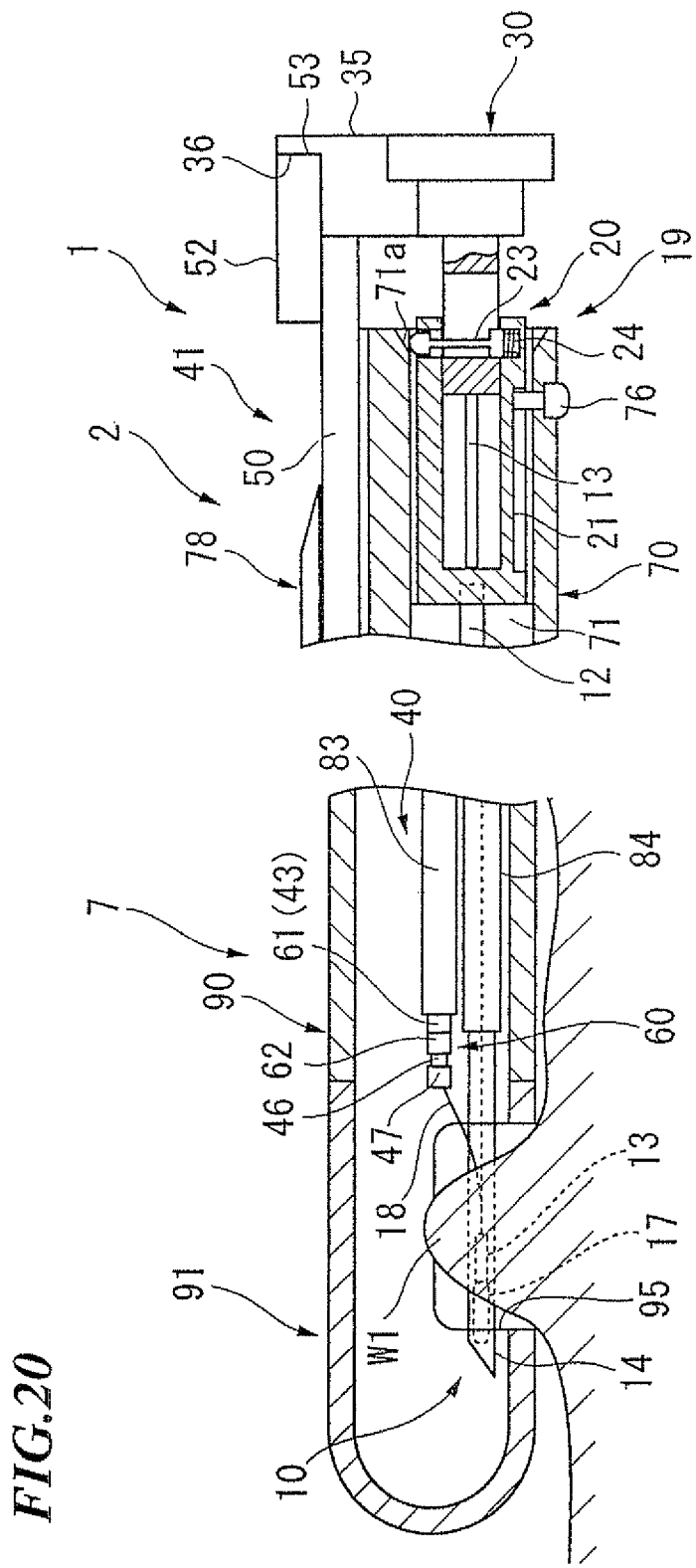
FIG. 20 is a side view showing a state in which a connection between the pressing handle and a puncture handle is broken.

As shown in FIG. 20, when the needle bodies 14 reach the position of penetrating the biomedical tissue W1 (i.e., a second position), almost all of the puncture handle 20 is inside the housing portion 70. At this time, the linking pin 23 is buried inside the puncture handle 20 due to the tapered surface 71a of the insertion hole 71. As a result, the link between the pressing handle 30 and the puncture handle 20 is released. Note that the operation up to this point is the same when the puncture handle 20 is made to move forward instead of the pressing handle 30.

Figure 21:
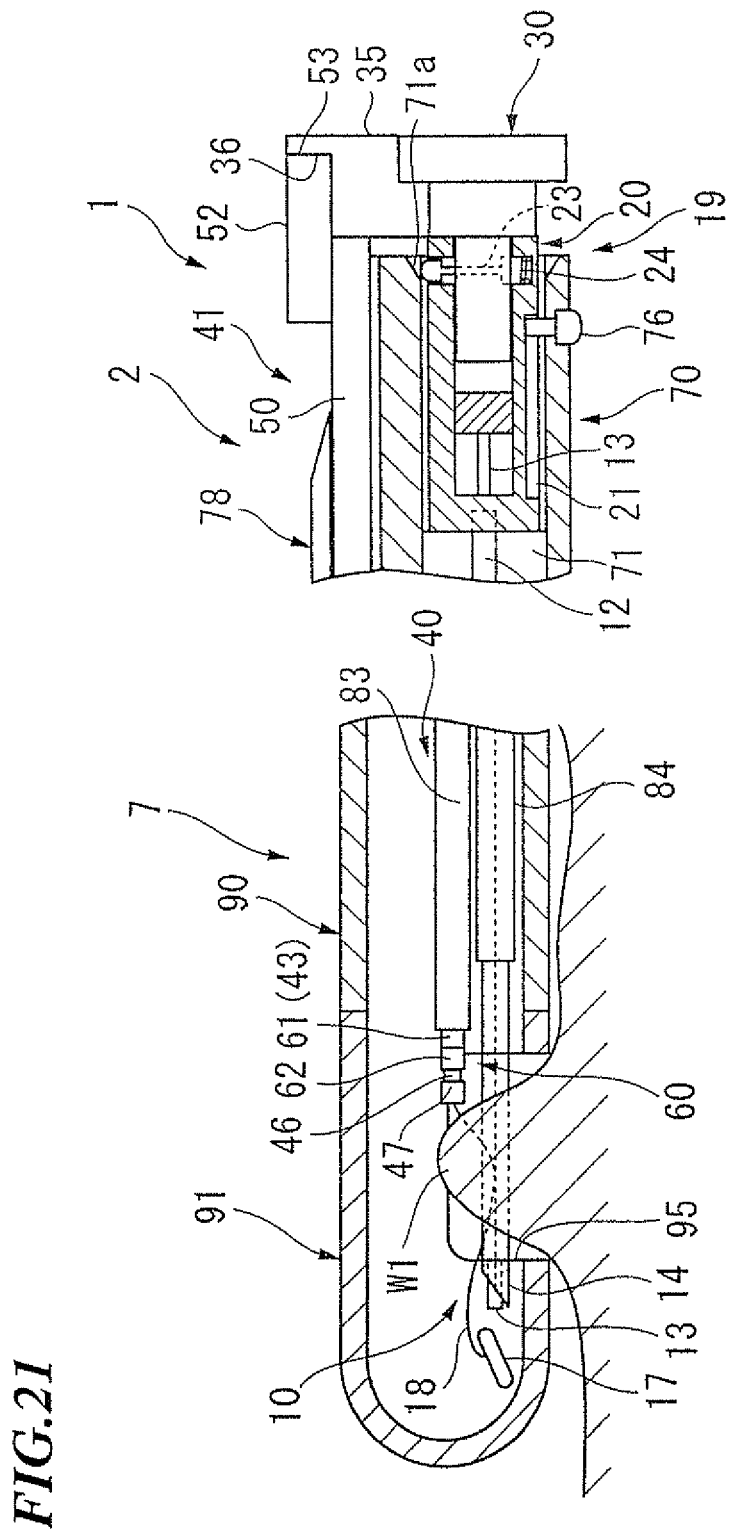
FIG. 21 is a view showing a state when the pressing handle is moved forward to its maximum.

If the pressing handle 30 is pushed in even after the respective needle bodies 14 have arrived at the second position, then because the puncture handle 20 remains stopped due to the link having been released, the pushers 13 move forward relative to the needle bodies 14. As a result, as shown in FIG. 21 the respective holding members 17 inside the respective needle bodies 14 are pushed out, and are discharged on the side of one side portion of the biomedical tissue W1. In addition, because the state of connection with the ligature tool 40 is maintained, the ligature tool 40 moves forward in connection with the pressing handle 30, and the stopper 46 approaches the other side portion of the biomedical tissue W1. Note that the positions of the pressing handle 30 and pushers 13 and of the ligature tool 40 at this time are taken as a third position.

Once each of the holding members 17 has been pushed out from the needle bodies 14, the pressing handle 30 is pulled back. As it moves in the backwards direction, because the engagement between the linking member 35 and the finger piece portion 52 is released, only the pressing handle 30 is pulled backwards and the pushers 13 remain housed inside the needle bodies 14.

Figure 22:
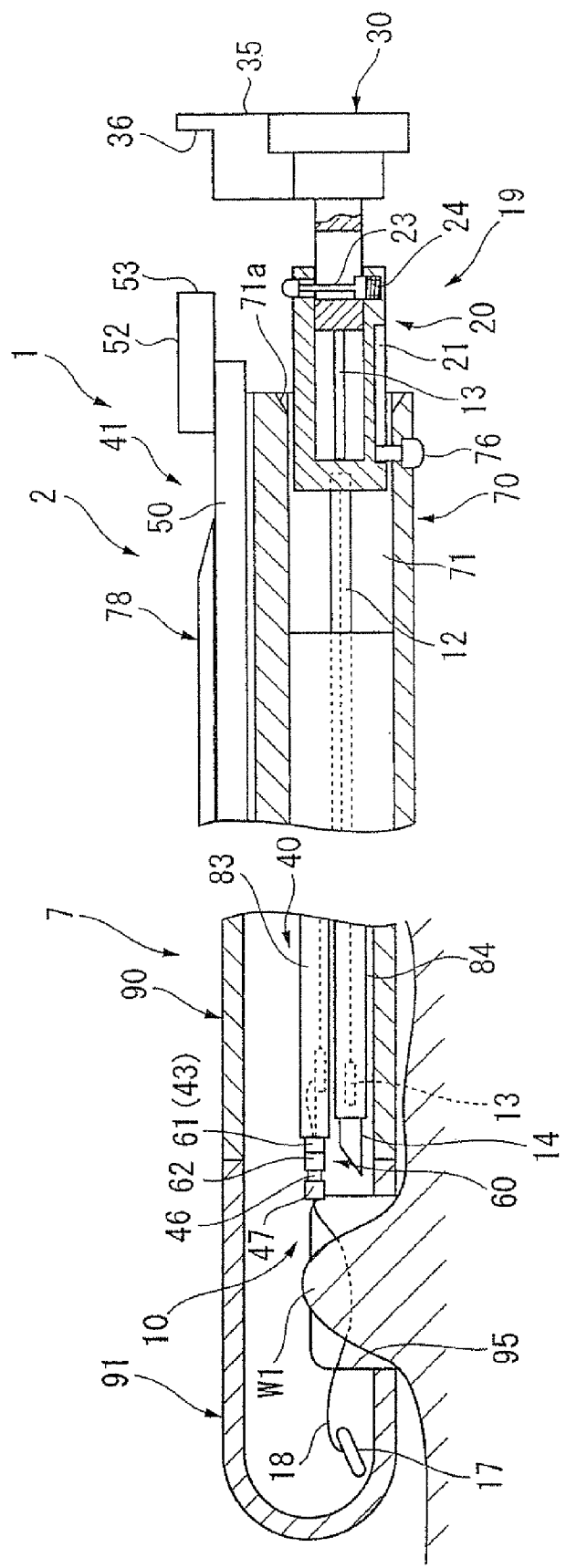
FIG. 22 is a view showing a state when the pressing handle is pulled back.

When the pressing handle 30 has been pulled back a predetermined amount, a distal end of the slit 34 (see FIG. 4) engages with the linking pin 23, and the puncture handle 20 becomes caught by the pressing handle 30 so as to begin to move backwards. At this time, the linking pin 23 that has been pushed by the tapered surface 71a gradually comes out so that the pressing handle 30 and the puncture handle 20 are linked together. As a result, the puncture handle 20 is pulled back in conjunction with the pressing handle 30, and the pushers 13 and needle bodies 14 move backwards simultaneously. As shown in FIG. 22, if the pressing handle 30 is then pulled back to its initial position, then the puncture handle 20 is also pulled back to its initial position and during this the respective needle bodies 14 are pulled out from the biomedical tissue W1. The holding member 17 is left at one side portion of the biomedical tissue W1, and the ligature thread 18 is inserted so as to penetrate both side portions of the biomedical tissue W1.

Figure 23:
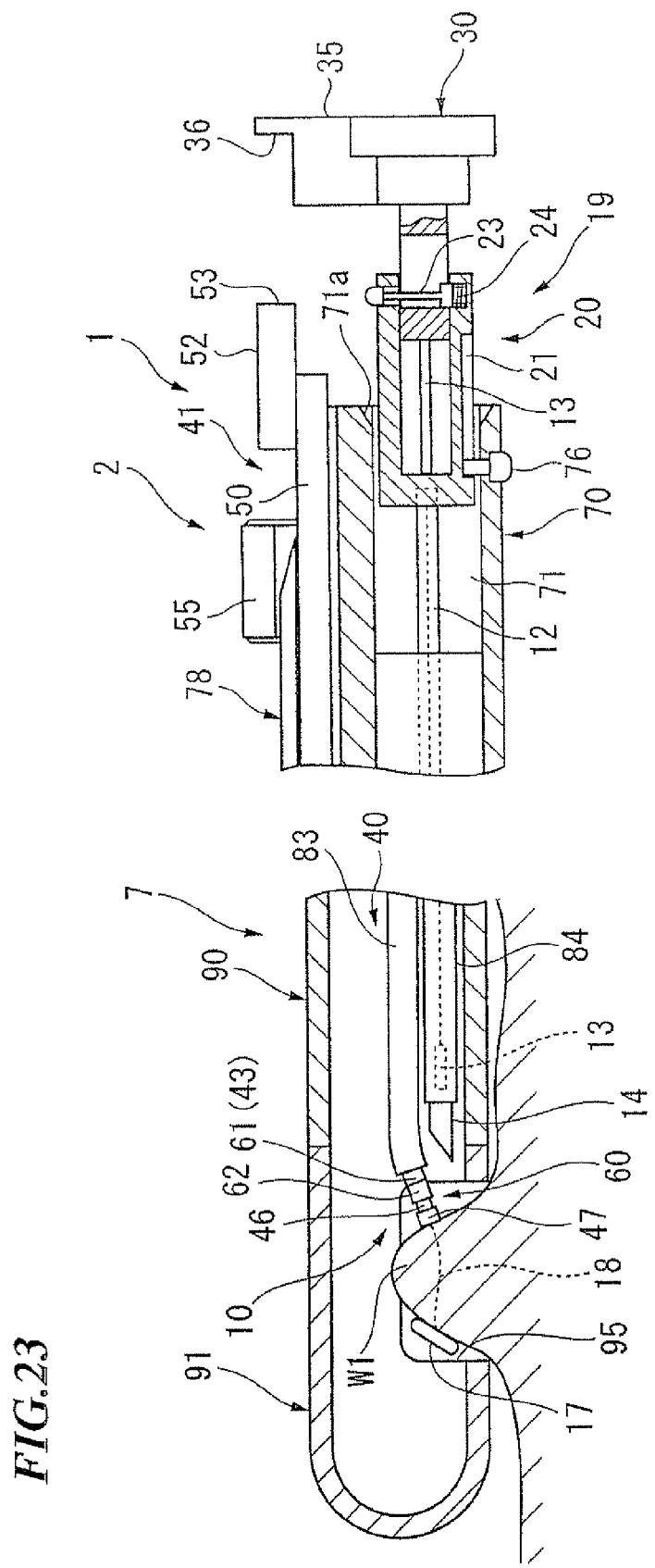
FIG. 23 is a view showing an operation during ligaturing.

Next, the ligature tool shown in FIG. 5 is operated, and the biomedical tissue W1 is ligatured by the holding member 17 and the stopper 46. Firstly, the ligature handle 55 is pulled back along the slit 54. The operating wire 44 that is fixed to the ligature handle 55 moves backwards and the hook 45 pulls the ligature thread 18. As a result, as shown in FIG. 23, the holding member 17 that is attached to an end portion of the ligature wire 18 is drawn towards the stopper 47 side, and is pressed against one side portion of the biomedical tissue W1. Because the position of the stopper 47 does not move, it is sandwiched by the holding member 17 and the stopper 46 so that the biomedical tissue W1 is ligatured.

Figure 24:
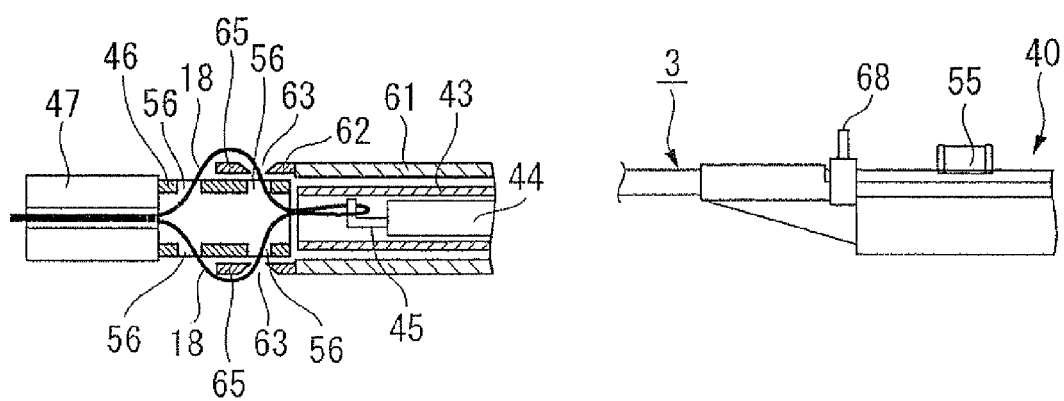
FIG. 24 is a view showing an operation of a cutter.
Figure 25:
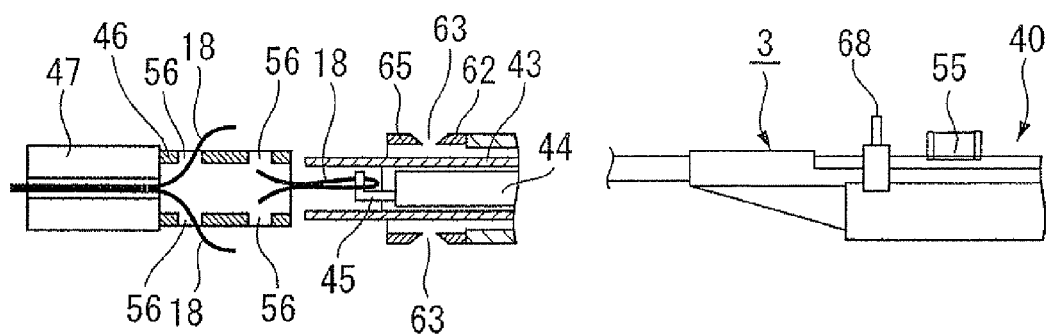
FIG. 25 is a view showing a state in which a ligature thread is cut by the cutter FIG. 26 a schematic view showing ligatured biomedical tissue.

When the biomedical tissue W1 has been ligatured, excess ligature thread 18 is cut. Namely, the cutter handle 68 shown in FIG. 24 is pulled so that the cutter sheath 61 is moved backwards. The cutter portion 62 is moved backwards and the blade portion 65 is moved so as to cover the through holes 56 so that, as shown in FIG. 25, the ligature thread 18 is cut.

Figure 26:
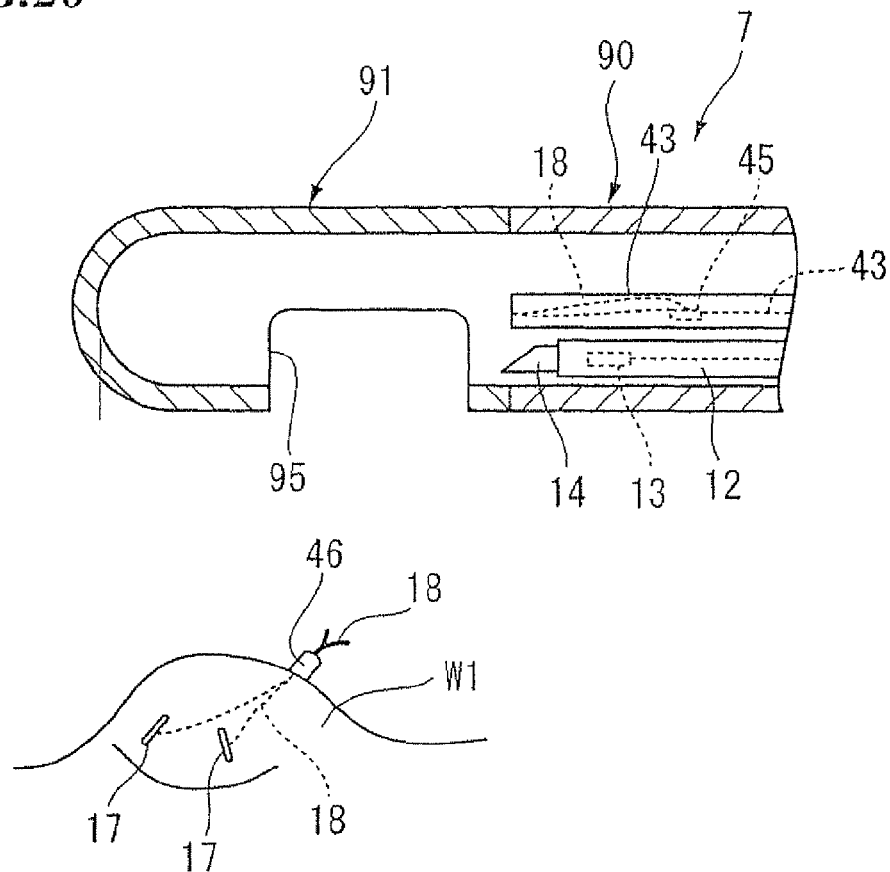

Thereafter, once the suction by the endoscope 6 has stopped, the overtube 7 is pulled out from the body cavity and the treatment is ended. As shown in FIG. 26, the biomedical tissue W1 is ligatured by two holding members 17 and the stopper 47 and a bulging state thereof is maintained.

According to this embodiment, because there are provided a puncture needle 10 that punctures the biomedical tissue W1, and a ligature tool 40 that ligatures the biomedical tissue W1 that has been penetrated by ligature thread 18, and because the ligature tool operation unit 41 having the respective handles 20, 30, and 55 is provided integrally, an operation can be performed by a single operator. In particular, because the puncture needle 10 and ligature tool 40 move in conjunction with each other, the operation is simplified. Furthermore, when the puncture needle 10 is made to puncture, because the respective needle bodies 14 and pushers 13 as well as the ligature tool 40 are linked together, there is no pulling out of the ligature thread 18, and it is possible to insert the ligature thread 18 reliably into the biomedical tissue W1.

Moreover, because the pressing handle 30 and the puncture handle 20 are linked by the linking pin 23, which forms a first linking device, between the first position and the second position, so that if one of the handle 20 and the handle 30 is moved backwards or forwards then the other of the handle 20 and the handle 30 is also moved backwards or forwards in the same direction, and because this link is released at the second position, the advancing of the puncture needle 10 and the subsequent pushing out of the holding member 17 can be performed using a simple structure in a single operation.

Furthermore, when the pressing handle 20 is moved forwards, because the linking member 35, which forms a second linking device, is engaged with the ligature tool 40 between the first position and the second position, it is possible to link the ligature tool 40 using a simple structure. Accordingly, simply by operating the pressing handle 30 it is possible to perform an operation to move the ligature tool 40 forwards or backwards. This interconnected operation continues until the pressing handle 30 arrives at the third position. Note that the linking member 35 also has a role of preventing the ligature tool 40 from coming out of the slide receiving portion 78.

By using the engaging screw 76, a structure can be formed in which the puncture needle operation unit 19 is freely removable from the housing 3. In addition, by using the engaging screw 76 the amount of movement of the puncture needle operation unit 19 can be controlled and the operation unit 19 can be prevented from coming out or rotating. Therefore, handling of the puncture needle operation unit 19 is simplified.

Because the colliding portion 81 is formed by a notch provided in the slide receiving portion 78, and because this colliding portion 81 acts as a stopper in the forward movement direction of the ligature tool 40, it is possible to control the forward movement of the ligature tool 40 using a simple structure.

Because the grip 77 of the housing 3 is inclined diagonally forwards, it is easy to apply force when moving each of the handles 20, 30, 55, and 68 as well as the ligature tool 40 forwards.

Because the pins 97 are provided in the distal end tube 91 of the overtube 7, it is possible to connect the distal end tube 91 such that the side aperture 95 and the needle bodies 14 are always in a fixed orientation.

In addition, if treatment is conducted using this type of ligature and suture device for medical application 1, then ligaturing of biomedical tissue W1 can be conducted rapidly and reliably.

Note that, in FIG. 13, the pins 97 are provided in the engaging portion 96 of the distal end tube 91, however, it is also possible to provide a concave receiving portion in the engaging portion 96, and to provide an engaging protrusion that engages with this receiving portion in the tube main body 90. The engaging protrusion in this case can also be used as a guide member that guides the forwards or backwards movement of the needle bodies 14.

Figure 27:
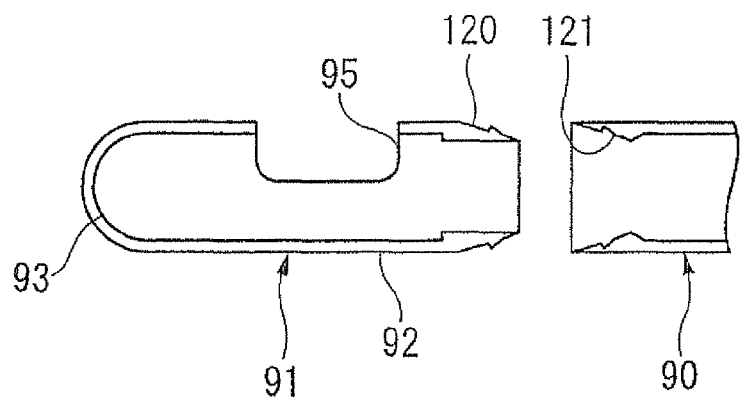
FIG. 27 a side view showing a state in which the distal end tube is separated from the tube main body.

Moreover, in this embodiment, in order to simplify the installation of the holding member 17 and the like, the distal end tube 91 of the overtube 7 is made freely removable from the tube main body 90 using the rotating ring 101, however, other engaging devices may also be used. For example, as shown in FIG. 27, saw tooth shaped protrusions 120 can be provided in a ring on an outer circumference of a base end portion of the distal end tube 91, and receiving portions 121 that engage with the protrusions 120 can be provided on an inner circumferential surface of a distal end aperture of the tube main body 90. If the protrusions 120 are manufactured using elastically deformable members, then the distal end tube 91 can be removed from or attached to the tube main body 90 simply by pulling or pushing the distal end tube 91 in the axial direction.

Figure 28:
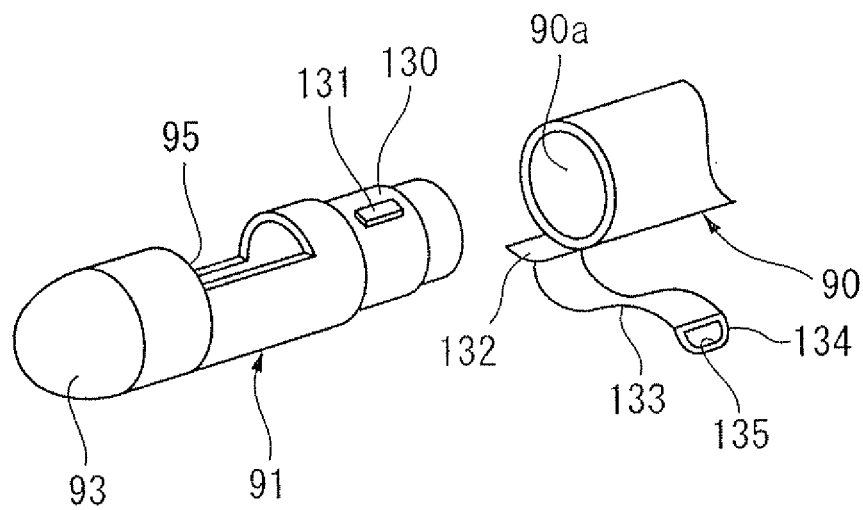
FIG. 28 is a perspective view showing a state in which the distal end tube is separated from the tube main body.
Figure 29:
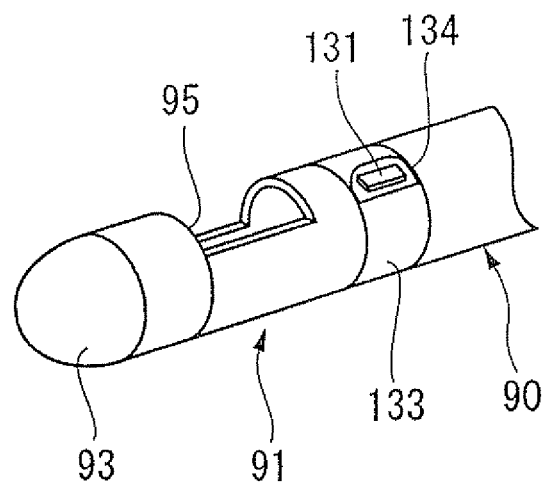
FIG. 29 is a perspective view showing a state in which the distal end tube is that it onto the tube main body.

Moreover, as shown in FIG. 28, it is also possible to provide a contracted diameter portion 130 at the base end portion of the distal end tube 91, and to provide a protrusion 131 at one location on the outer circumference of this contracted diameter portion 130. A portion of the distal end aperture in 90a of the tube main body 90 is extended in the axial direction so that an extended portion 132 is formed, and an end portion of a rubber belt 133 is fixed to this extended portion 132. An engaging member 134 is fixed to the other end portion of the rubber belt 133. A hole 135 that engages with the protrusion 131 is provided in the engaging member 134. As shown in FIG. 29, in a state in which the distal end tube 91 is placed against the distal end aperture of the tube main body 90, the rubber belt 133 is wound around the outer circumferential surface of the contracted diameter portion 130, and the hole 135 is engaged with the protrusion 131. In this case, positioning in the rotation direction of the distal end tube 91 is also possible.

(Second Embodiment)

A second embodiment of the present invention will be described with reference to FIGS. 30 to 33. Note that component elements that are the same as those in the first embodiment are given the same symbols. In addition, any description that is duplicated from the first embodiment is omitted.

Figure 30:
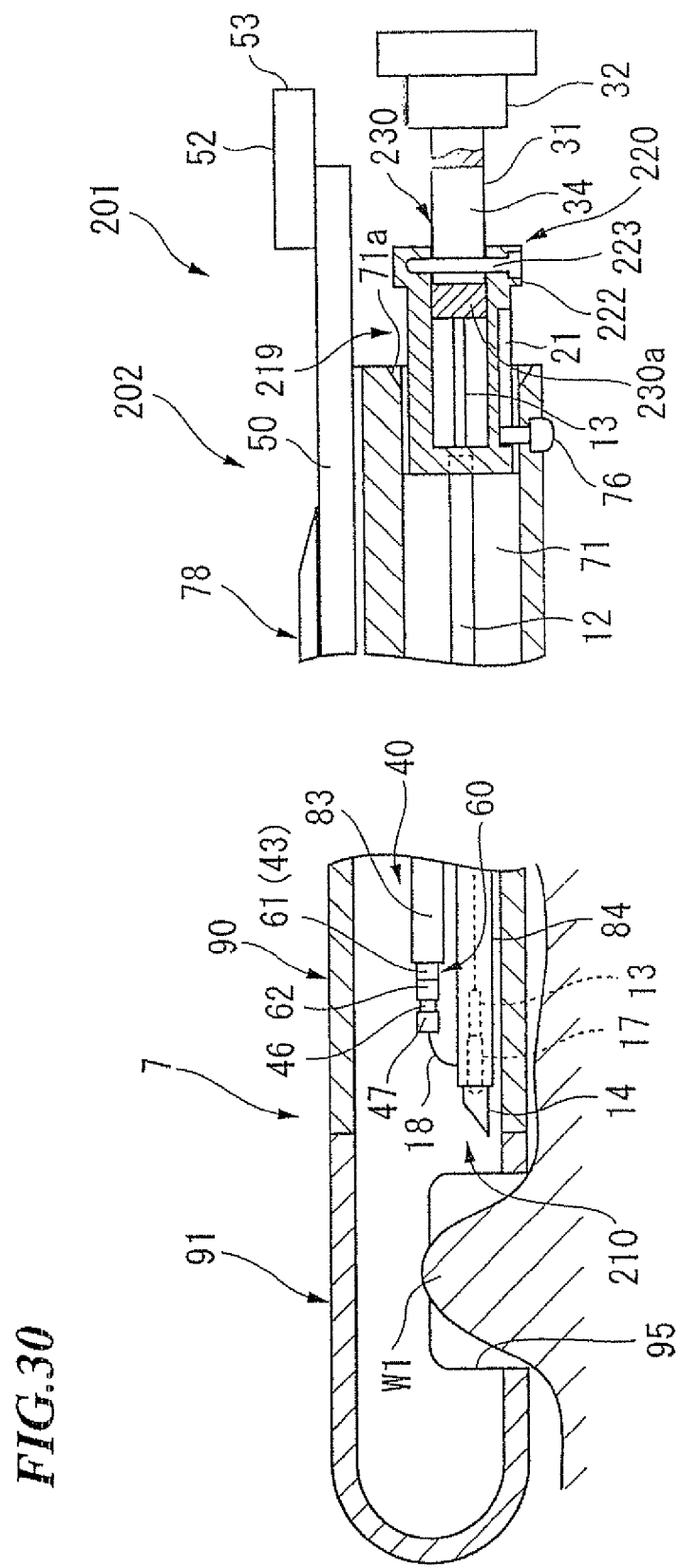
FIG. 30 is a view showing an operation of a ligature and suture device for medical application according to a second embodiment of the present invention, and is a side view showing the layout in an initial state.

As shown in FIG. 30, a ligature and suture device for medical application 201 has an operation section 202. An overtube 7 is attached via a tube 4 and an endoscope insertion portion 5 (see FIG. 1) to a distal end of the operation section 202.

The operation section 202 has a housing 3, and a puncture needle operation unit 219 for a puncture needle 210 is installed in a housing portion 78 of the housing 3 so as to be able to move freely backwards and forwards. In addition, the ligature tool operation unit 41 is installed in a slide receiving portion 78 so as to be able to move freely backwards and forwards.

Here, in the puncture needle operation unit 219, a pin 223 is fixed inside an enlarged diameter portion 222 on a base end side of a puncture handle 220. The pin 223 is placed inside a slit 34 of a pressing handle 230, and is able to engage with a distal end portion 230a of the pressing handle 230. Furthermore, the pressing handle 230 is able to move backwards and forwards independently from the ligature tool 40. Note that the remainder of the structure of the ligature and suture device for medical application 201 is the same as that of the first embodiment.

Figure 31:
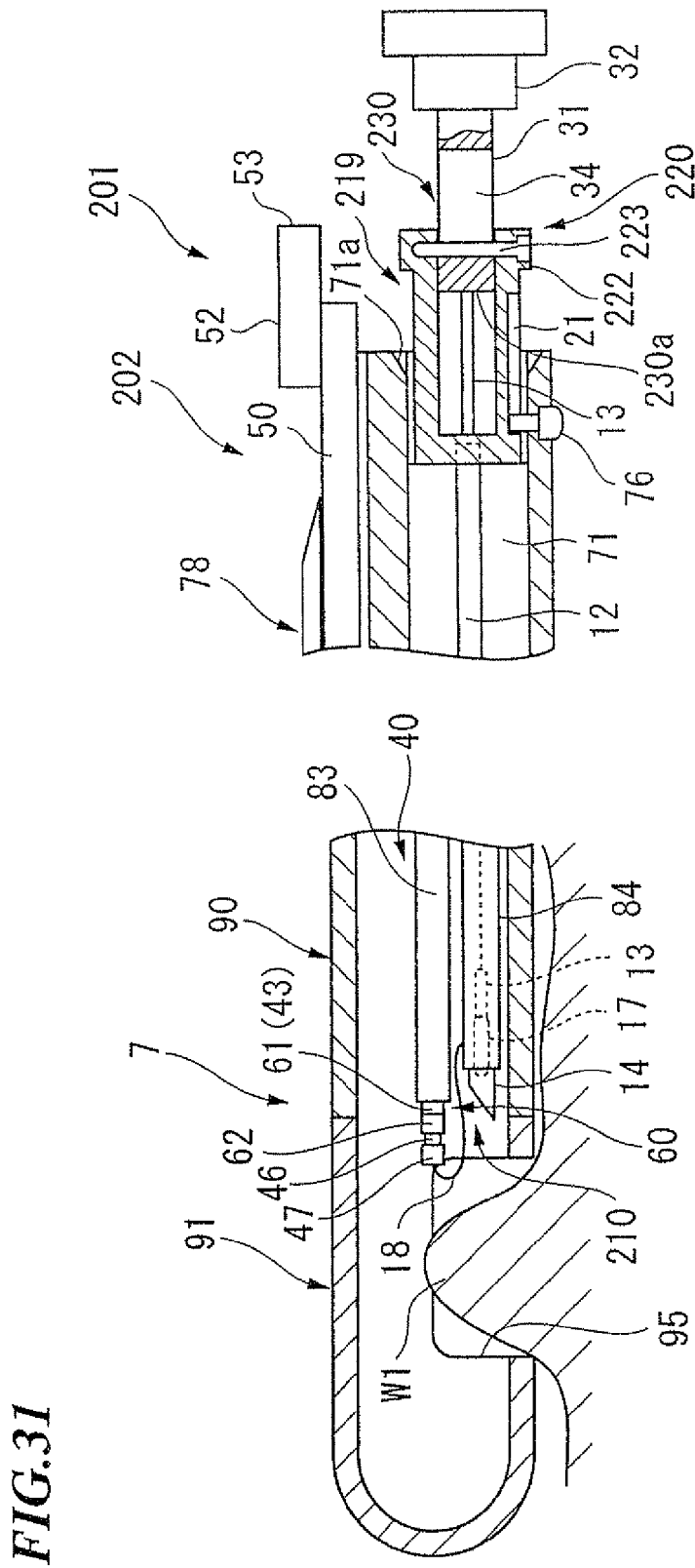
FIG. 31 is an enlarged view showing principal portions of a ligature.
Figure 32:
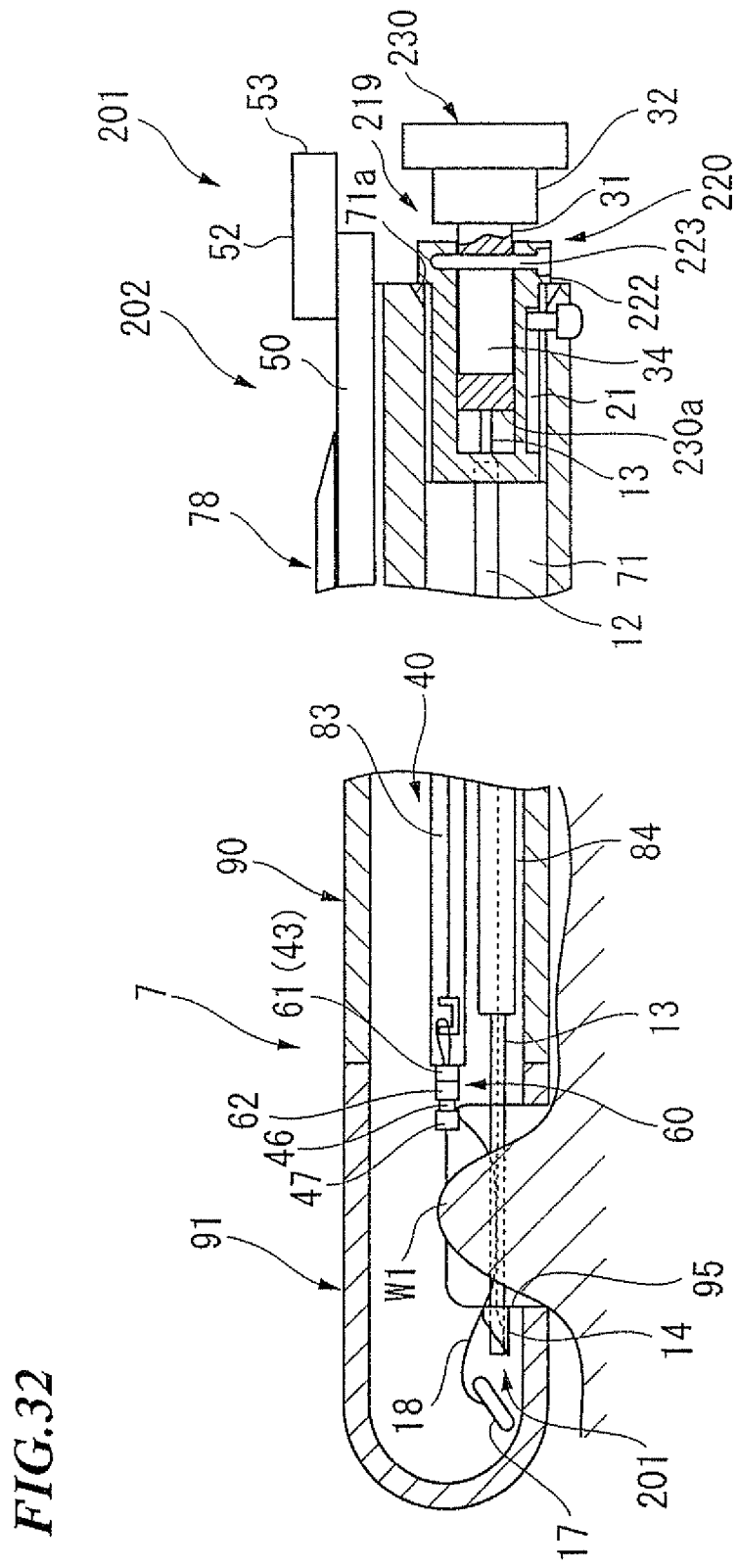
FIG. 32 is an in view showing a state in which the ligature tool is moved forward.

When biomedical tissue W1 is ligatured using the ligature and suture device for medical application 201, the biomedical tissue W1 is suctioned inside the overtube 7 inside a body cavity. Subsequently, as shown in FIG. 31, the ligature tool operation unit 41 is moved forwards so that the ligature sheath 43 is moved forwards, and the stopper 47 is placed adjacent to the biomedical tissue W1. As a result, the distance between the stopper 47 and the respective holding members 17 is contracted.

Next, the puncture handle 220 is moved forward and the two needle bodies 14 at the distal ends of each inner sheath 12 are moved forward simultaneously. At this time, because the pressing handle 230 is engaged by the pin 223, the pressing handle 230 moves forward together with the puncture handle 220, and the pushers 13 also move forward the same distance as the needle bodies 14. Because of this, the pin 223 functions as a device for linking the pressing handle 230 while the puncture handle 220 is moved forward from the first position to the second position.

Once the distal end of each needle body 14 has penetrated the biomedical tissue W1 and arrived at the second position, the puncture handle 220 is no longer operated and the pressing handle 230 is moved forward. As shown in FIG. 3, each pusher 13 pushes the two holding members 17 out from the respective needle bodies 14.

Figure 33:
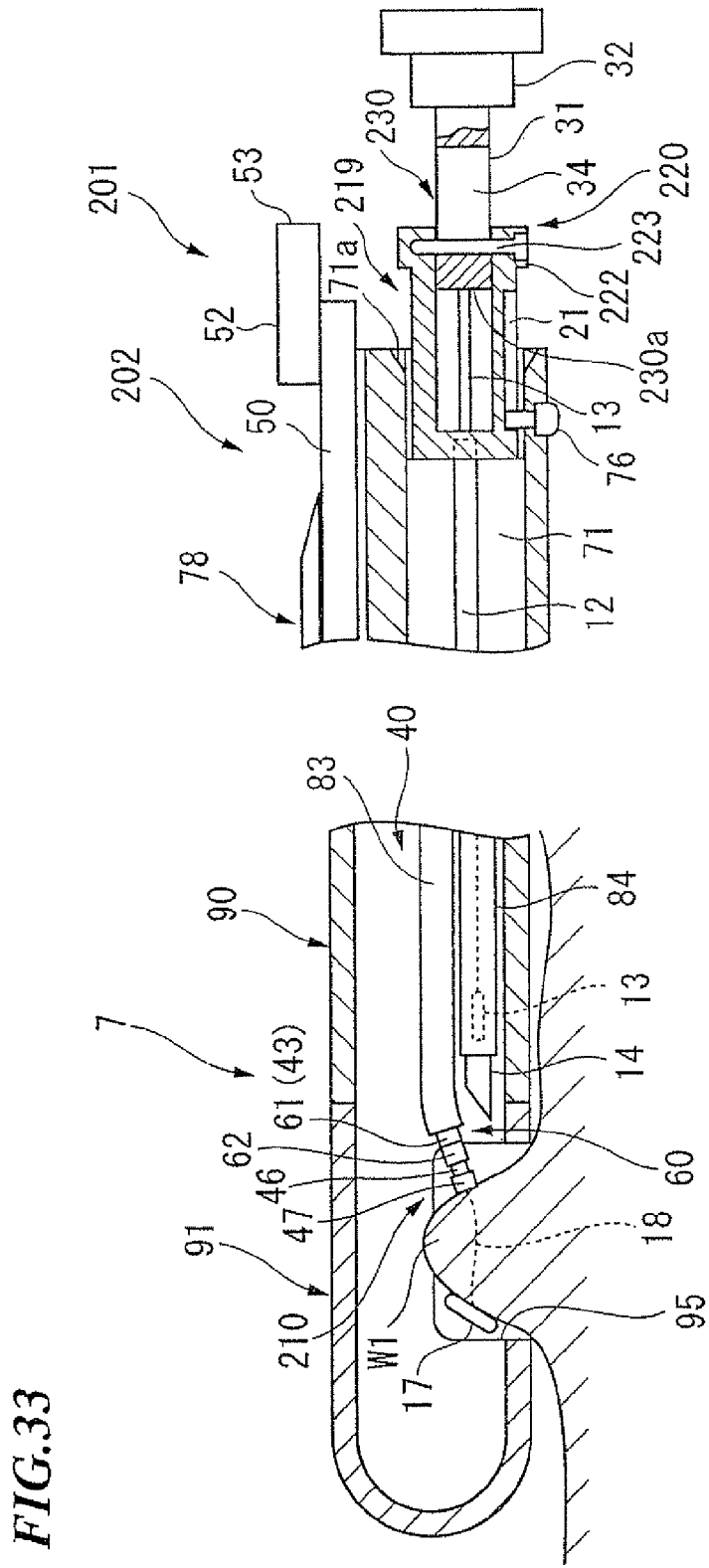
FIG. 33 is a view showing an operation to make a ligature after the pressing handle has been moved backwards.

Next, after the pressing handle 230 has been returned to its initial position, the puncture handle 230 is returned to its initial position (see FIG. 33). As a result, each pusher 13 is pulled back, and, in addition, each pusher 13 and each needle body 14 is pulled out of the biomedical tissue W1. Moreover, while the main body portion 50 of the ligature tool operation unit 41 is in a fixed state, the ligature handle 55 is moved backwards, and the ligature thread 18 is pulled by the hook 45, so that the biomedical tissue W1 is sandwiched by the holding members 17 and the stoppers 47 and is ligatured. After the ligaturing, the cutter handle 68 (see FIG. 24) is moved backwards, and excess ligaturing thread 18 is cut.

In this embodiment, because the ligature tool 40 is provided that operates inside a body cavity and in the vicinity of the biomedical tissue W1, treatment from puncturing to ligaturing can be performed rapidly. Moreover, because it is possible to move the needle bodies 14 of the puncture needle 210, the pushers 13, the ligature sheath 43 of the ligature tool 40, and the hook 45 independently backwards and forwards, the degree of operating freedom is increased.

(Third Embodiment)

Figure 35:
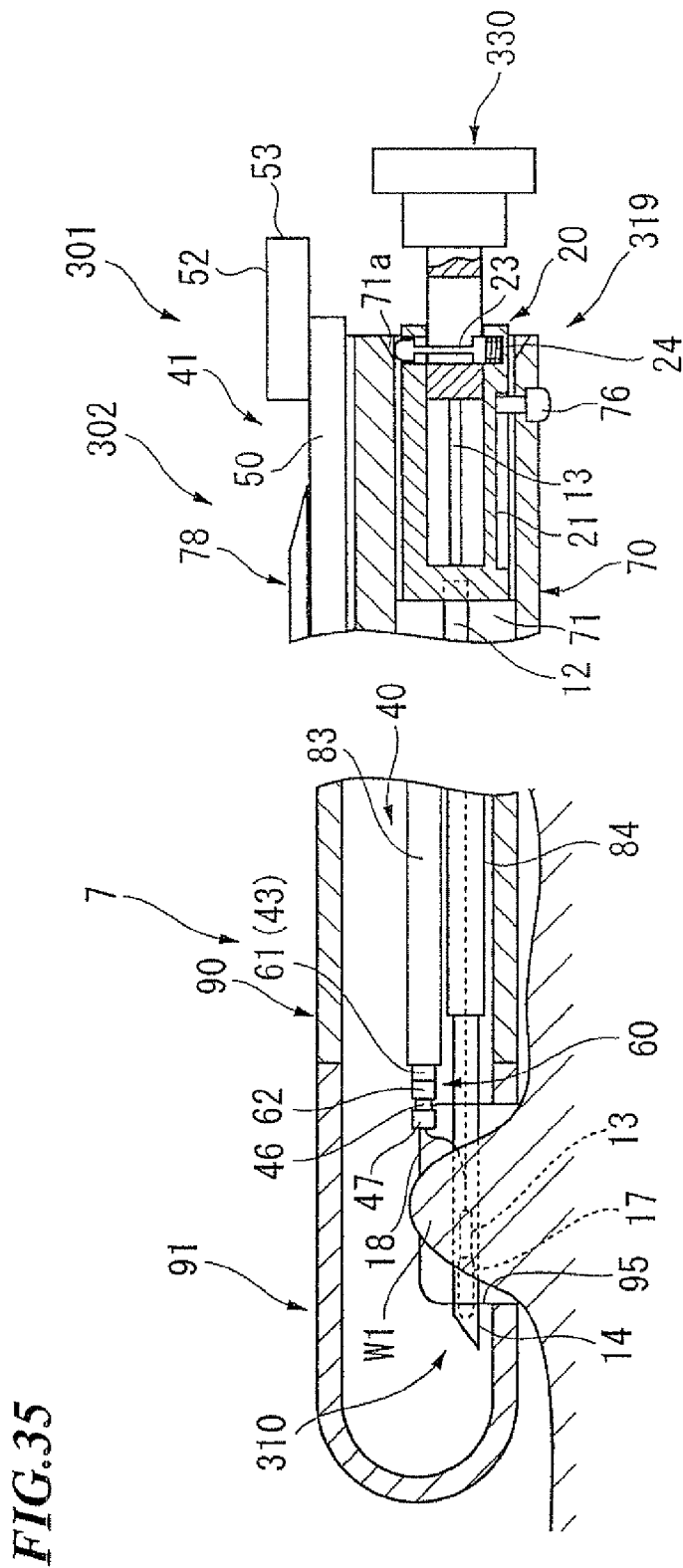
FIG. 35 is a view showing a state in which the pressing handle is moved forward and the connection between the pressing handle and the puncture handle is broken.
Figure 36:
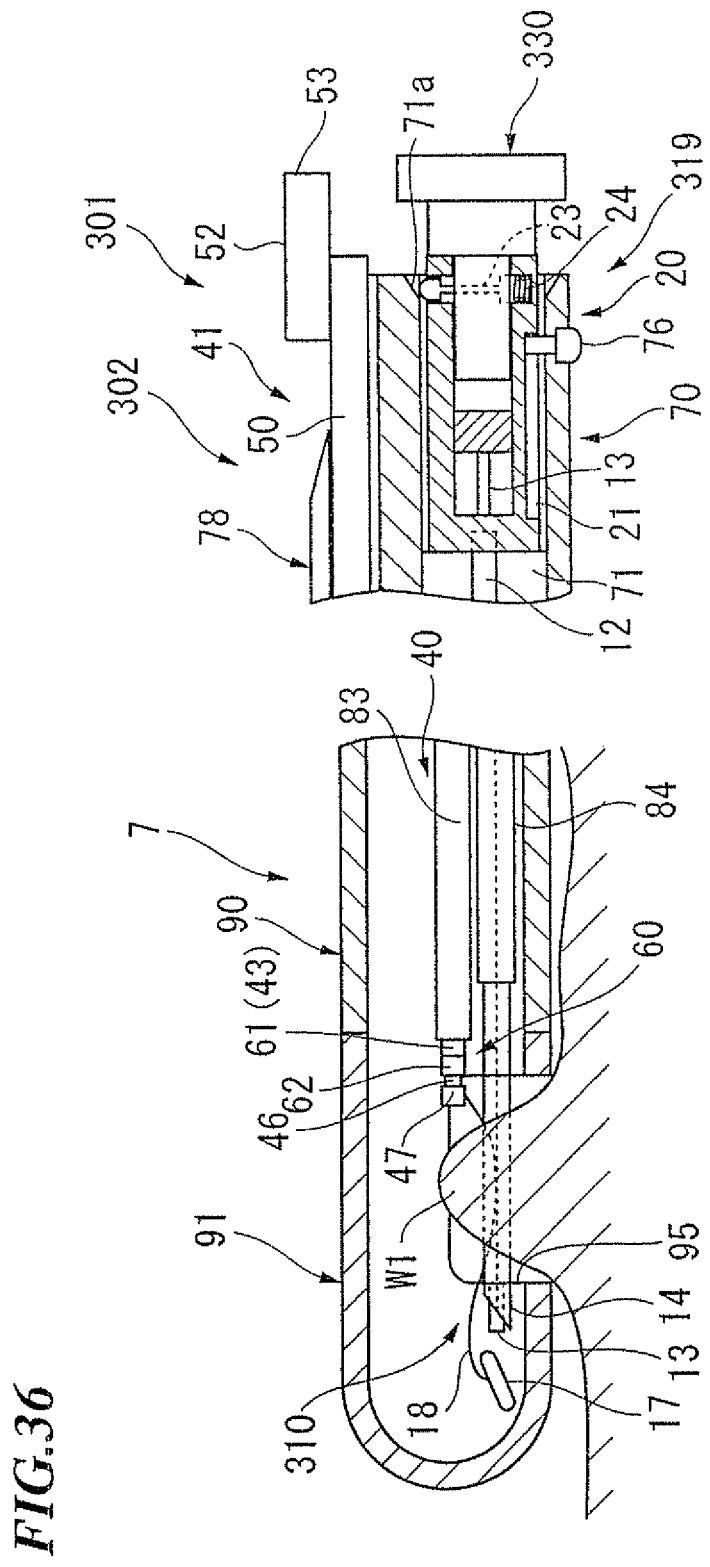
FIG. 36 is a view showing a state in which the pressing handle is moved forward to its maximum.

A third embodiment of the present invention will be described with reference to FIGS. 34 to 36. Note that component elements that are the same as those in each of the above embodiments are given the same symbols. In addition, any description that is duplicated from the above embodiments is omitted.

Figure 34:
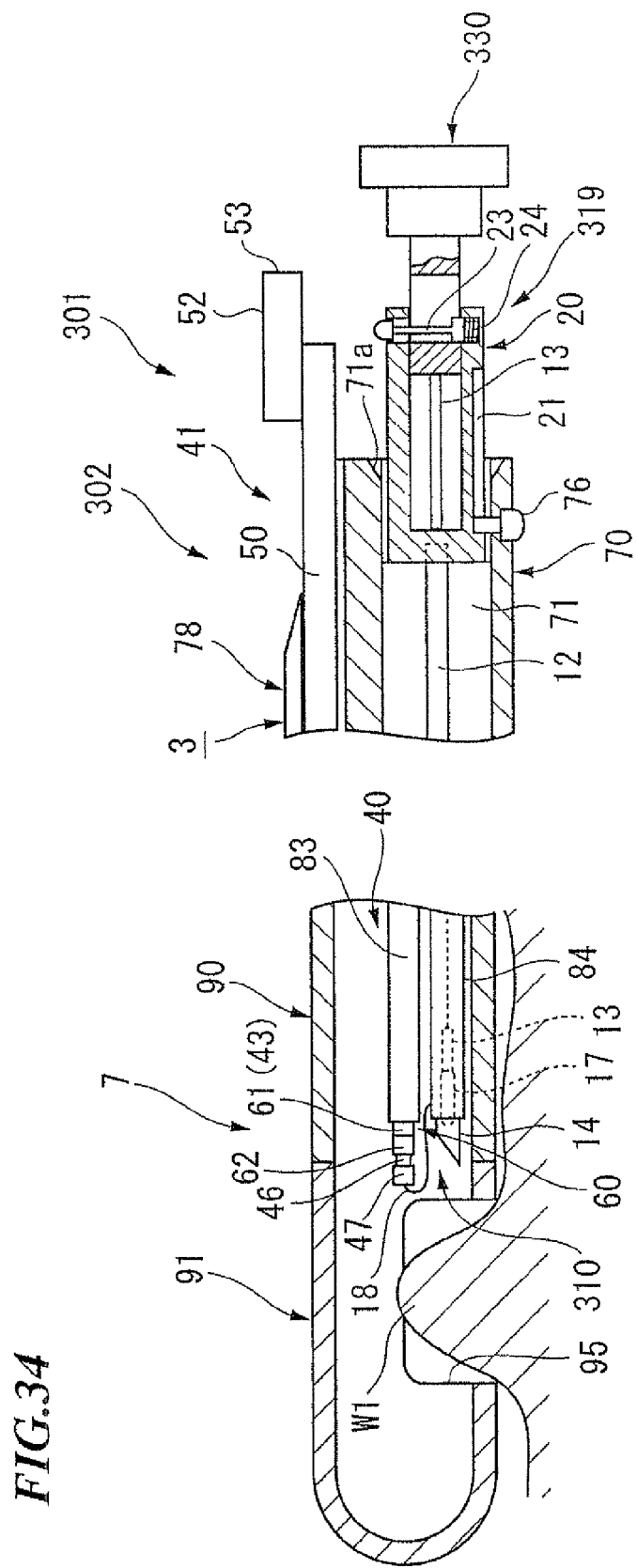
FIG. 34 is a view showing an operation of a ligature and suture device for medical application according to a third embodiment of the present invention, and is a side view showing the layout in an initial state.

As shown in FIG. 34, in a ligature and suture device for medical application 301 having an operation section 302, a puncture needle operation unit 319 for a puncture needle 310 is inserted in a housing portion 70 of a housing 3. The puncture needle operation unit 319 is provided with a linking pin 23 that engages and links the puncture handle 20 with a pressing handle 330, however, the pressing handle 330 and the ligature tool 40 are able to move backwards and forwards independently. Note that, in FIG. 34, a state is shown in which the ligature tool 40 is pressed in by a predetermined amount. The remaining component elements of the ligature and suture device for medical application 301 are the same as those in the first embodiment.

When biomedical tissue W1 is ligatured using the ligature and suture device for medical application 301, the biomedical tissue W1 is suctioned inside the overtube 7 inside a body cavity. Subsequently, the ligature tool 40 is moved forwards so that the stopper 47 is moved forwards to a position near the side aperture 95 on the distal end side of the needle bodies 14.

Next, the pressing handle 330 is moved forward. Because the puncture handle 20 is linked to the pressing handle 330 by the linking pin 23, the respective needle bodies 14 are moved forward towards the biomedical tissue W1 together with the respective pushers 13. As shown in FIG. 35, when the respective needle bodies 14 arrive at the second position where they penetrate the biomedical tissue W1, because the linking pin 23 is moved so that the link between the pressing handle 330 and the puncture handle 20 is released, subsequently only the pressing handle 330 is moved forward. Next, as shown in FIG. 36, at the farthest forward position of the pressing handle 330, the respective pushers 13 push the respective holding members 17 out from the respective needle bodies 14. Note that, during this time, the ligature tool 40 is in a stopped state.

After this, if the pressing handle 330 is pulled back, only the pressing handle 330 moves backwards as far as the second position where the linking pin 23 once again operates, and once the pressing handle 330 passes the second position, the puncture handle 20 also moves backwards in conjunction with the pressing handle 330. In this manner, once each needle body 14 has been pulled out and the ligature thread 18 has been made to penetrate the biomedical tissue W1, the ligature handle 55 is moved backwards, the biomedical tissue W1 is ligatured, and excess ligature thread is cut using the cutter handle 68 (see FIG. 24).

In this embodiment, because the ligature tool 40 is provided that operates inside a body cavity and in the vicinity of the biomedical tissue W1, treatment from puncturing to ligaturing can be performed rapidly. Moreover, because the needle bodies 14 of the puncture needle 310 and, the pushers 13 are linked together when the biomedical tissue W1 is punctured and when the needle bodies 14 are removed from the biomedical tissue W1, the actions during this time can be performed in a single operation, so that operability is improved.

(Fourth Embodiment)

A fourth embodiment of the present invention will be described with reference to FIGS. 37 to 41. Note that component elements that are the same as those in each of the above embodiments are given the same symbols. In addition, any description that is duplicated from the above embodiments is omitted.

Figure 37:
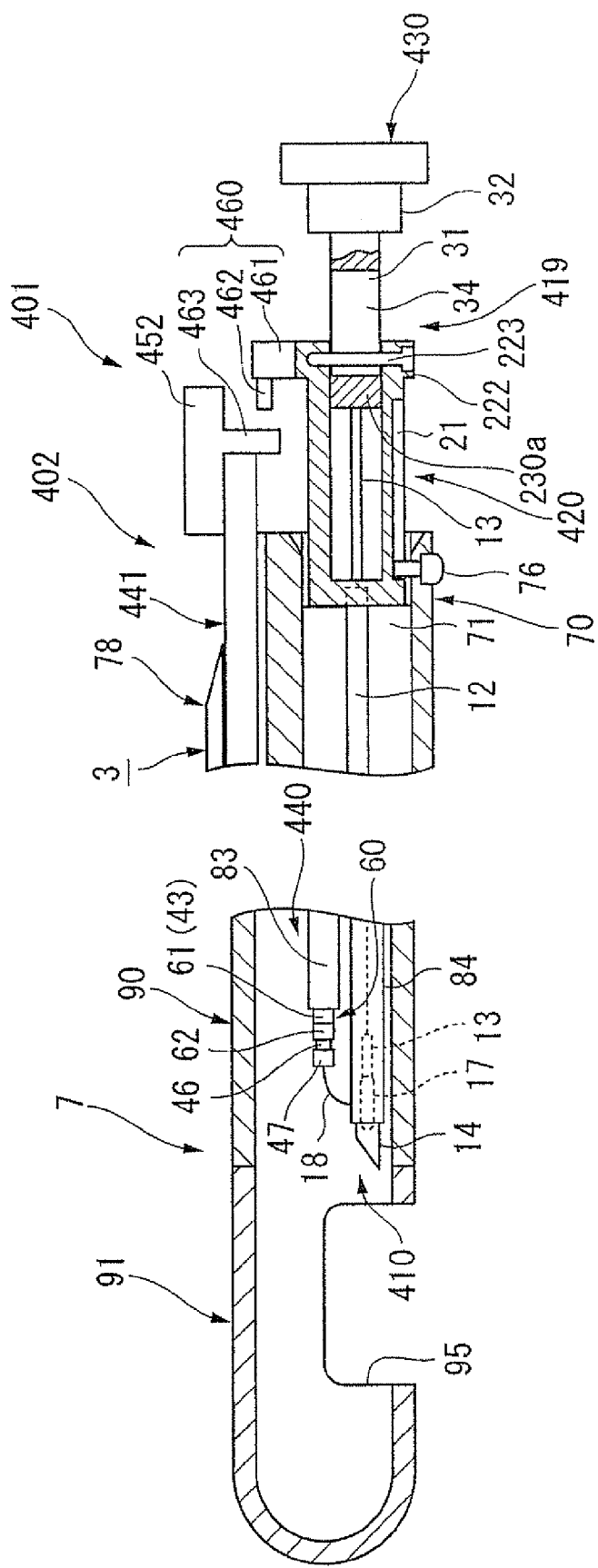
FIG. 37 is a view showing an operation of a ligature and suture device for medical application according to a fourth embodiment of the present invention, and is a side view showing the layout in an initial state.
Figure 38:
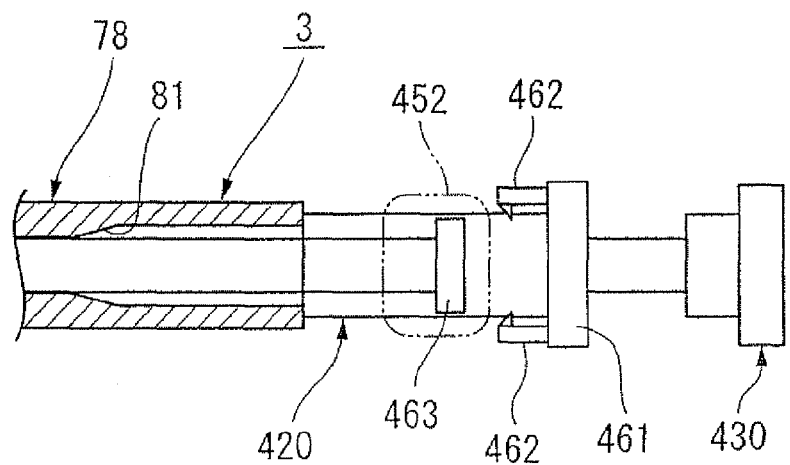
FIG. 38 is a top view of a base end side of the operation section.

As shown in FIG. 37, in a ligature and suture device for medical application 401 having an operation section 402, a puncture needle operation unit 419 for a puncture needle 410 is inserted in a housing portion 70 of a housing 3. In the puncture needle operation unit 419, a puncture handle 420 and a pressing handle 430 are able to move backwards and forwards independently. In addition, a linking device 460 that links the puncture handle 420 with a ligature tool 440 is provided. The linking device 460 is formed by an engaging claw 462 that extends in the distal end direction from a top portion of a supporting portion 461 that is attached to an enlarged diameter portion 222 of the puncture handle 420, and by an engaged portion 463 that extends downwards from a finger piece portion 452 of a ligature tool operation unit 441. As shown in FIG. 38, two of the engaging claws 462 are provided parallel with each other. Each of these can be elastically deformed, and distal ends thereof are bent so as to approach each other. The engaged portion 463 has a width and length that enables it to be engaged with the engaging claws 462.

The remaining component elements of the ligature and suture device for medical application 401 are the same as those in the first embodiment.

Figure 39:
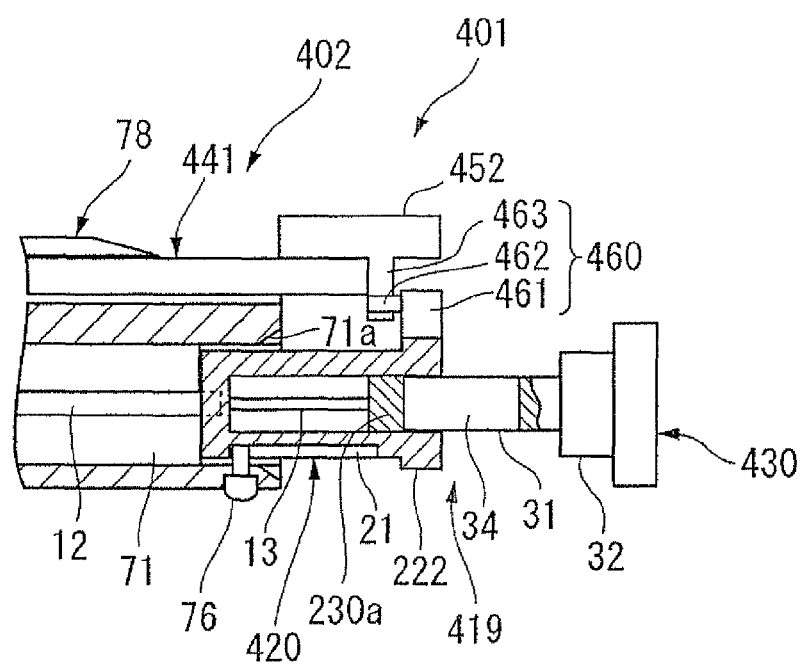
FIG. 39 is a side view showing a state in which the pressing handle is connected to the ligature tool.
Figure 40:
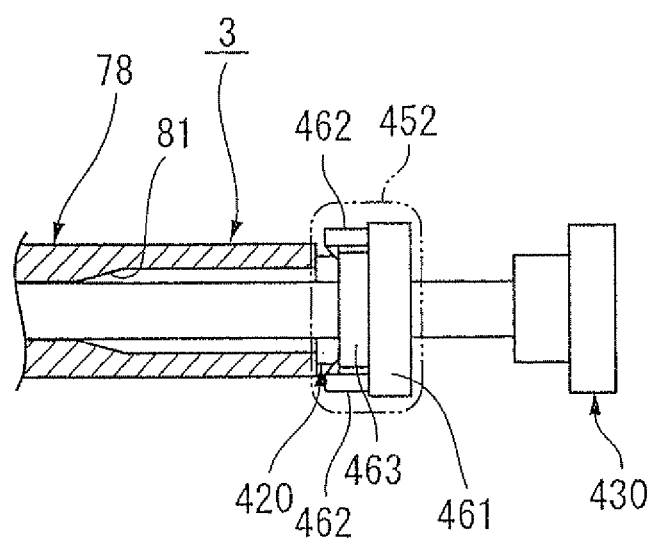
FIG. 40 is a plan view showing a state in which the pressing handle is connected to the ligature tool.

In this ligature and suture device for medical application 401, in an initial state, the puncture handle 420 is pulled out such that the engaging claw 462 is on the rear side of the engaged portion 463 of the ligature tool 440. If the puncture handle 420 is moved forward, the pressing handle 430 also moves forward in conjunction with this, so that, as a result, the needle bodies 14 and the pushers 13 move forwards simultaneously. Here, as shown in FIG. 39 and FIG. 40, once the puncture handle 420 has moved forward a predetermined length, the engaging claw 462 engages with the engaged portion 463, so that the puncture handle 420 and the ligature tool 440 are linked together. This predetermined length is a distance such that excess tensile force does not act on the ligature thread 18 between the holding members 17 inside the needle bodies 14 and the stopper 47.

Figure 41:
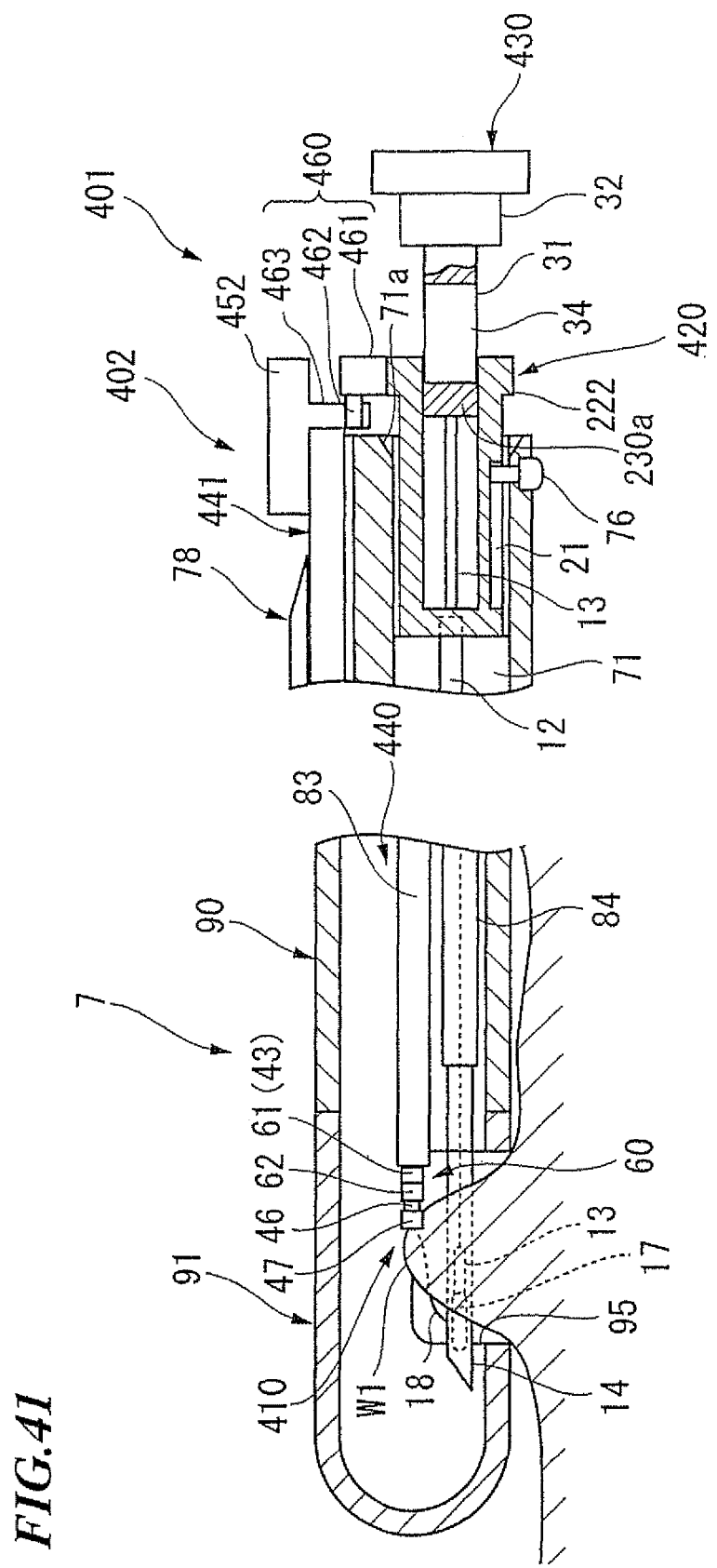
FIG. 41 is a view showing a state in which the ligature tool is moved forward.

When the puncture handle 420 is moved even further forward, the respective needle bodies 14, the respective pushers 13, the ligature tool 440, and the cutter 60 (see FIG. 1) are moved forwards simultaneously. As shown in FIG. 41, at the position where the puncture handle 420 comes up against the housing portion 70, each of the needle bodies 14 has penetrated the biomedical tissue W1. After this, if the pressing handle 430 is moved forward, only the respective pushers 13 are moved forward and the respective holding members 17 are pushed out.

Next, the pressing handle 330 is returned. Furthermore, after the connection between the puncture handle 420 and the ligature tool 440 is broken, the puncture handle 420 is pulled back, and the respective needle bodies 14 are removed from the biomedical tissue W1. The ligature handle 55 is further pulled so that the biomedical tissue W1 is ligatured and excess ligature thread 18 is cut by the cutter portion 62 (see FIG. 24).

In this embodiment, because the ligature tool 440 is provided that operates inside a body cavity and in the vicinity of the biomedical tissue W1, treatment from puncturing to ligaturing can be performed rapidly. Moreover, by using the linking device 460, the puncture handle 420 and the ligature tool 440 can be simply and reliably linked. Accordingly, when puncturing the biomedical tissue W1, by operating the puncture handle 420, the needle bodies 14, the pushers 13, the ligature tool 440, and the cutter portion 62 can be moved together. Therefore, the actions during this time can be performed in a single operation, so that operability is improved.

Furthermore, if a puncture is made in error and the needle bodies 14 are removed and the puncture is made again, because it is possible to move the ligature tool 440 backwards and forwards simply by operating the puncture handle 420, the operation is made easy.

(Fifth Embodiment)

Figure 43:
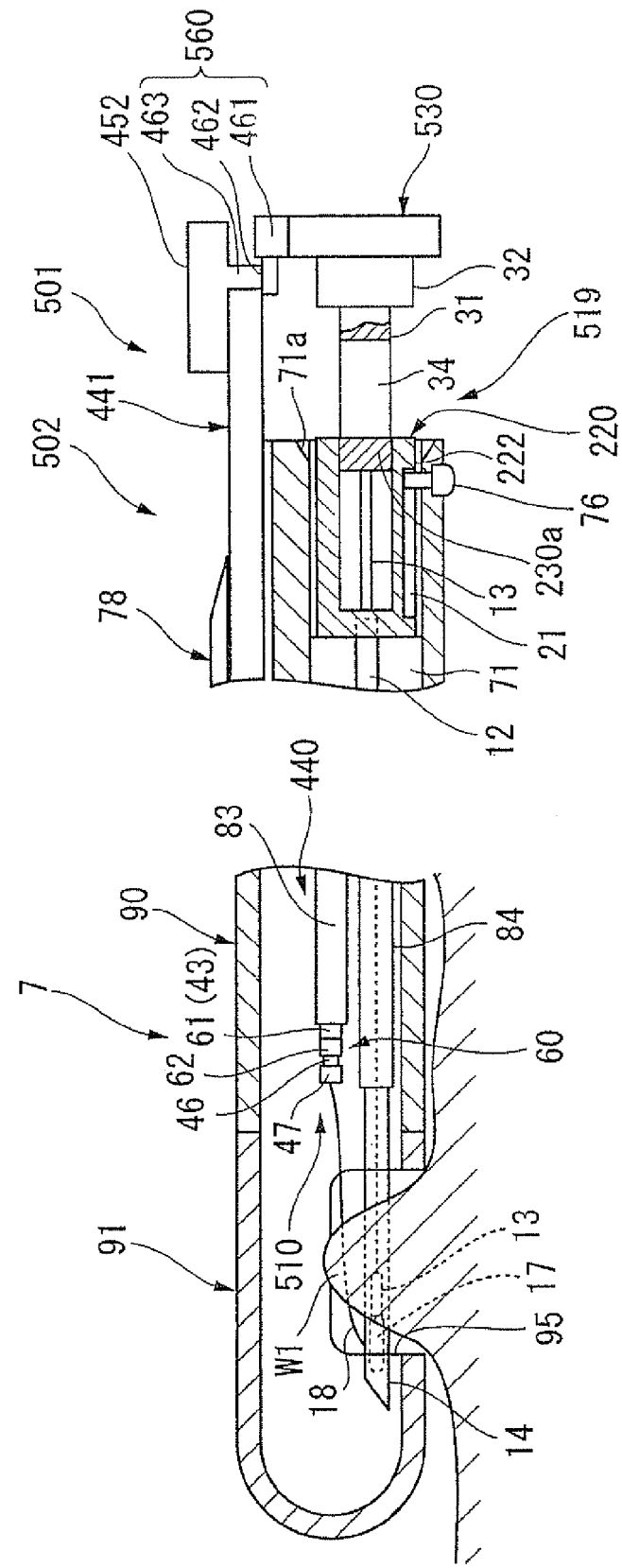
FIG. 43 is a view showing a state in which only the needle bodies are moved forward.
Figure 44:
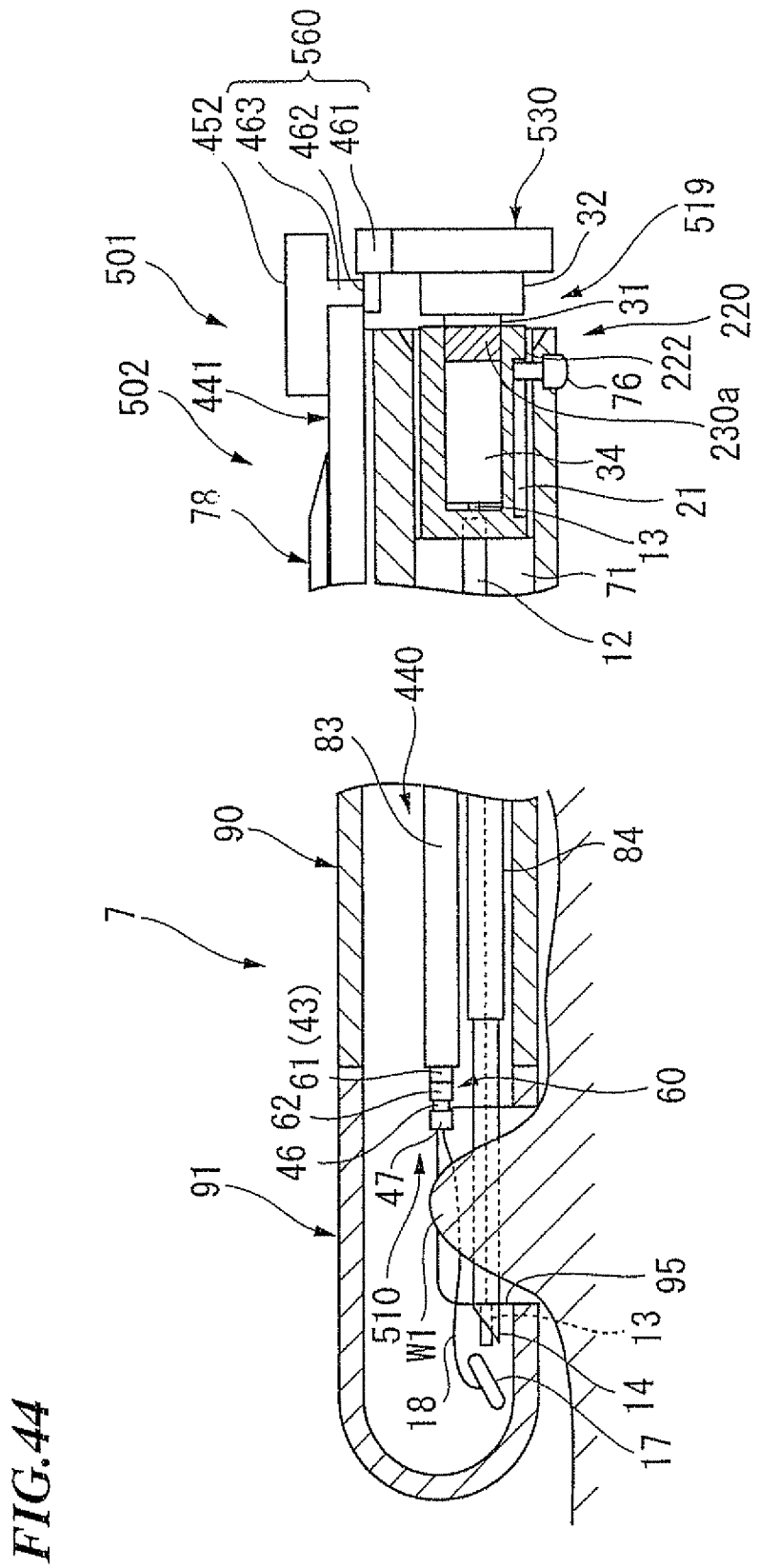
FIG. 44 is a view showing a state in which only the pushers are moved forward.

A fifth embodiment of the present invention will be described with reference to FIGS. 42 to 44. Note that component elements that are the same as those in each of the above embodiments are given the same symbols. In addition, any description that is duplicated from the above embodiments is omitted.

Figure 42:
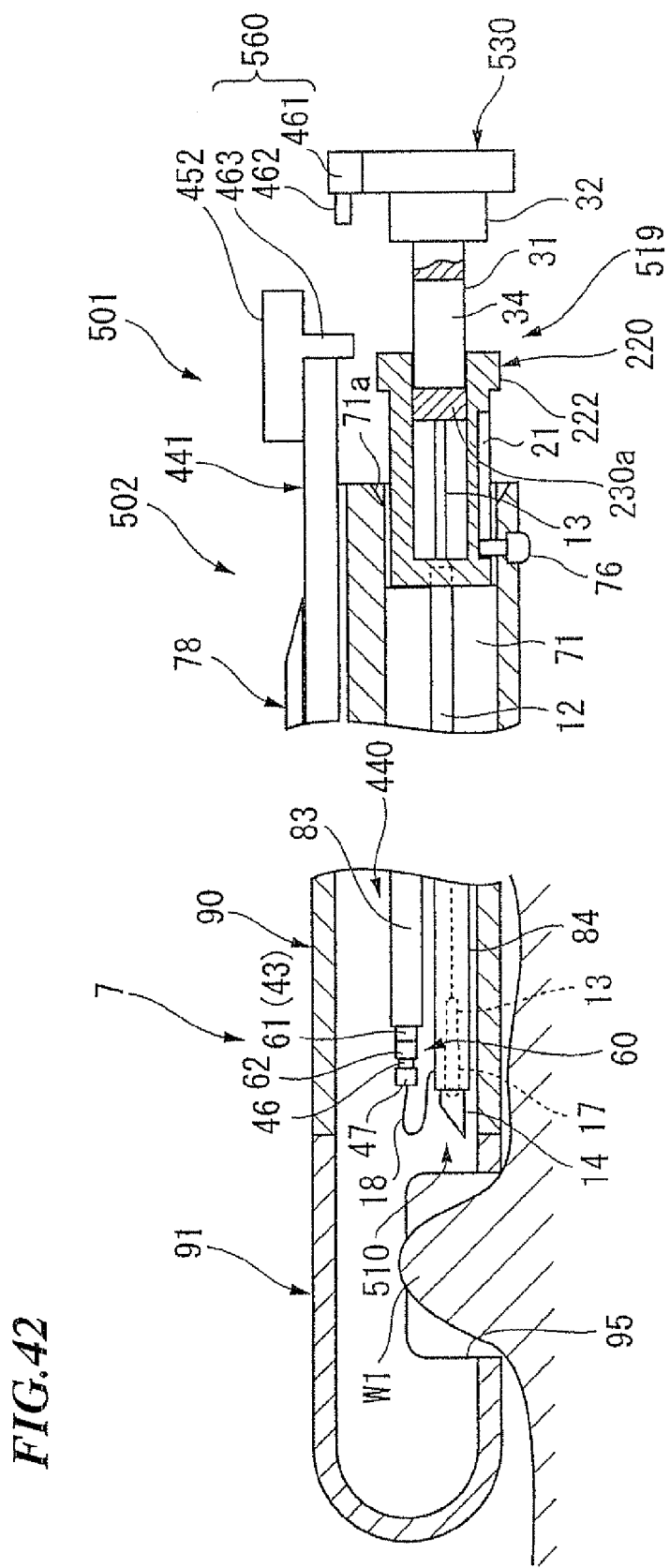
FIG. 42 is a view showing an operation of a ligature and suture device for medical application according to a fifth embodiment of the present invention, and is a side view showing the layout in an initial state.

As shown in FIG. 42, a ligature and suture device for medical application 501 has an operation section 502, and is further provided with a linking device 560 that links a pressing handle 530 with the ligature tool 440. The linking device 560 is formed by the engaging claw 462 and the supporting portion 461 thereof that are provided in the pressing handle 530, and by the engaged portion 463 that is provided in the finger piece portion 452 of the ligature tool operation unit 441. The remaining component elements are the same as those in the fifth embodiment In this ligature and suture device for medical application 501, by moving the puncture handle 220 forward, the pressing handle 530 is driven subordinately and the respective needle bodies 14 and respective pushers 13 are moved forward. At this time, before the puncture handle 220 is housed in the housing portion 70, as shown in FIG. 43, the pressing handle 530 and the ligature tool 440 are engaged by the linking device 560, and begin to move together. Moreover, as shown in FIG. 44, if the puncture handle 220 is moved forward as far as the third position, then the respective holding members 17 are pushed out from the respective needle bodies 14, and the stopper 47 is moved forward to a position adjacent to the biomedical tissue W1.

In this embodiment, because the ligature tool 440 is provided that operates inside a body cavity and in the vicinity of the biomedical tissue W1, treatment from puncturing to ligaturing can be performed rapidly. Moreover, by using the linking device 560, the pressing handle 430 and the ligature tool 440 can be simply and reliably linked. Accordingly, when puncturing the biomedical tissue W1, by operating the puncture handle 220, the needle bodies 14, the pushers 13, the ligature tool 440, and the cutter portion 62 can be moved together. Therefore, the actions during this time can be performed in a single operation, so that operability is improved.

(Sixth Embodiment)

A sixth embodiment of the present invention will be described with reference to FIGS. 45 to 50. Note that component elements that are the same as those in each of the above embodiments are given the same symbols. In addition, any description that is duplicated from the above embodiments is omitted.

Figure 45:
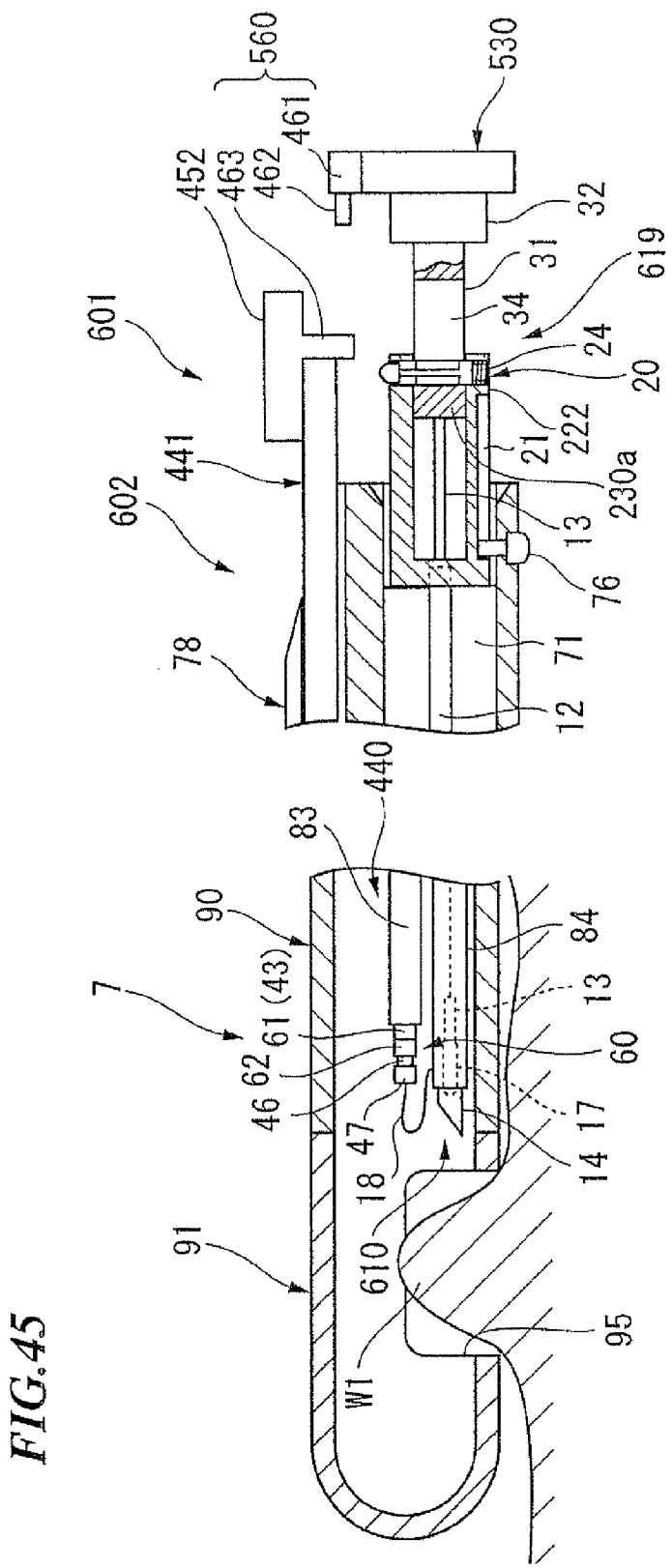
FIG. 45 is a view showing an operation of a ligature and suture device for medical application according to a sixth embodiment of the present invention, and is a side view showing the layout in an initial state.

As shown in FIG. 45, a ligature and suture device for medical application 601 has an operation section 602, and is further provided with the linking device 560 that connects the pressing handle 530 and the ligature tool 440. The remaining component elements are the same as those in the first embodiment.

In this ligature and suture device for medical application 601, in an initial state, the pressing handle 530 is pulled out to the first position, and the pressing handle 530 and the puncture handle 20 are linked by the linking pin 23. In addition, the engaged portion 463 of the ligature tool 440 is positioned closer to the distal end side than the engaging claw 462 of the pressing handle 530, so that both are independent of each other.

When ligaturing the biomedical tissue W1, firstly, the pressing handle 530 is moved forward. The puncture handle 20 moves forwarded in conjunction with the pressing handle 530, and the respective needle bodies 14 and the respective pushers 13 move forward. Furthermore, if the pressing handle 530 is pressed, the engaging claw 462 and the engaged portion 463 are engaged in a predetermined position, so that the ligature tool 440 is linked to the pressing handle 530. The distance of the movement of the pressing handle 530 from its initial position until it is linked to the puncture handle 20 is set within a range such that excess tensile force does not act on the ligature thread 18 between the respective holding members 17 and the stopper 47.

Figure 46:
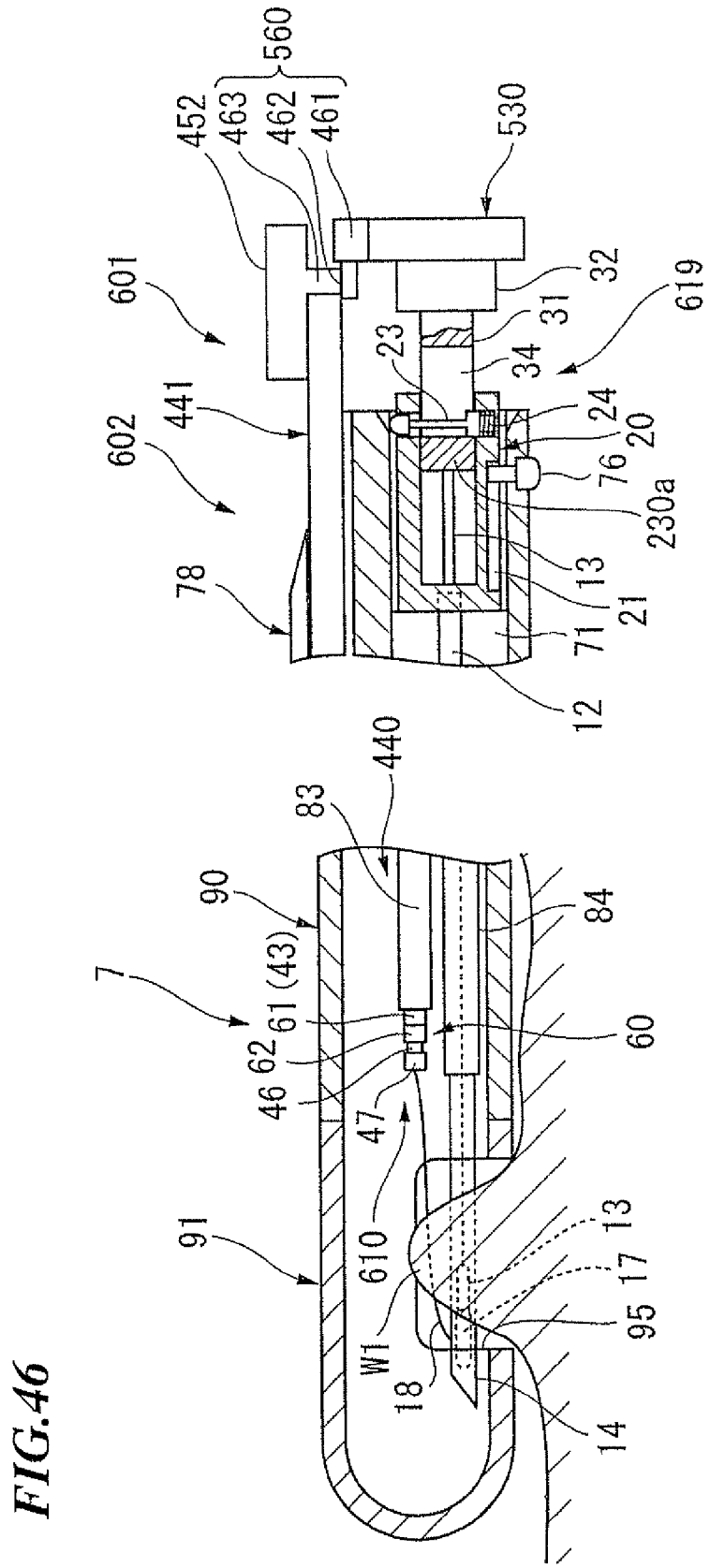
FIG. 46 is a view for showing a state in which the pressing handle, the puncture handle, and the ligature tool move together.

Moreover, as shown in FIG. 46, when the linking pin 23 of a puncture needle operation unit 619 is housed inside the housing portion 70 at the second position, the engagement between the pressing handle 530 and the puncture handle 20 is released. At this time, the respective needle bodies 14 have penetrated the biomedical tissue W1.

Figure 47:
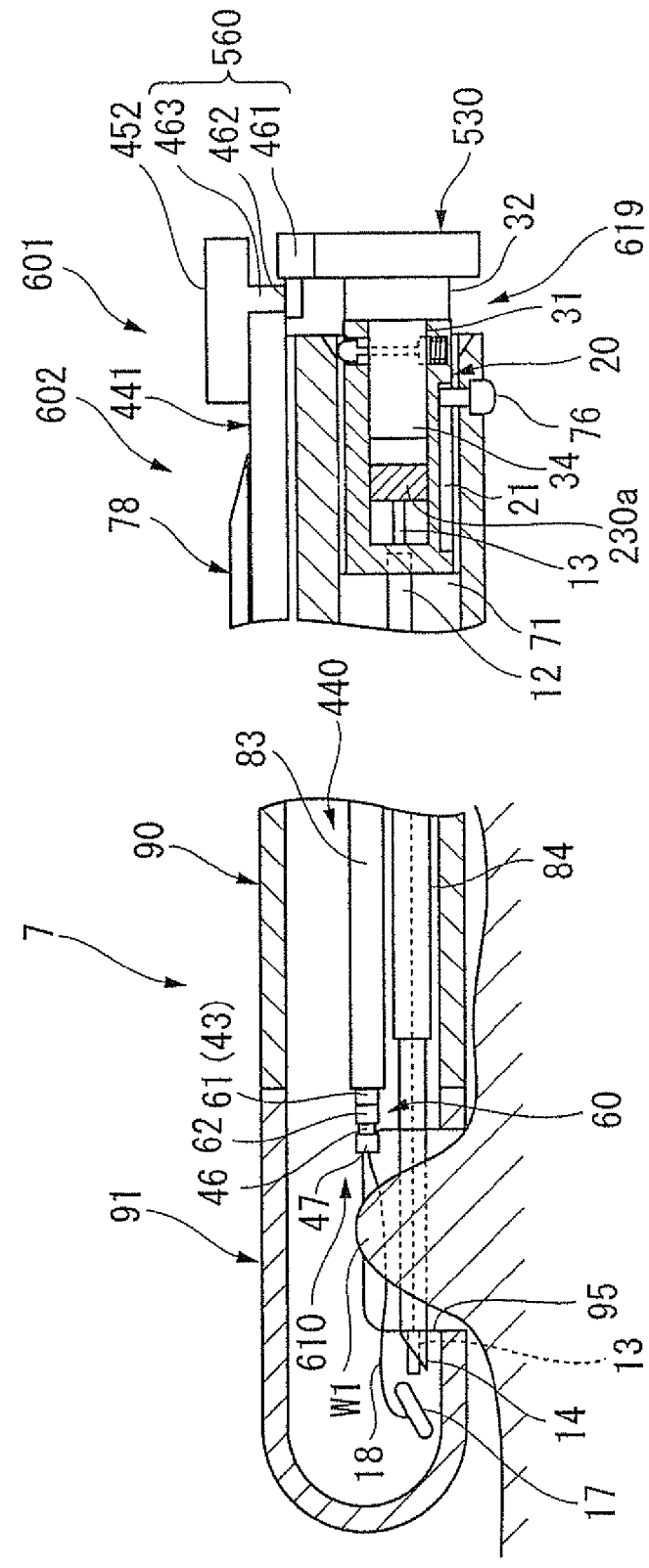
FIG. 47 is a view showing a state in which the pressing handle is moved forward to its maximum.

If the pressing handle 530 is moved forward even further, the ligature tool 440 moves forward in accordance with this. As shown in FIG. 47, when the engaged portion 463 comes against the base end surface of the housing portion 70, the respective pushers 13 push the respective holding members 17 out from the respective needle bodies 14.

Next, the pressing handle 530 is pulled backwards while releasing the engagement between the engaged portion 463 and the engaging claw 462. In the same way as in the first embodiment, after only the respective pushers 13 have moved backwards, the pressing handle 530 and the puncture handle 20 begin to move together, and the respective pushers 13 and the respective needle bodies 14 are removed from the biomedical tissue W1. By further operating the ligature tool 440 and the cutter 60 (see FIG. 24), the biomedical tissue W1 is ligatured and excess ligature thread 18 is cut.

In this embodiment, the same effects as those of the first embodiment are obtained. Furthermore, because the linking device 560 is provided, and the ligature tool 440 and the pressing handle 530 are linked, it is possible to move the needle bodies 14 backwards and forwards integrally with the ligature tool 440. Accordingly, for example, when installing the holding members 17 or the like, or when confirming the puncture position, a forwards or backwards movement can be easily performed.

Figure 48:
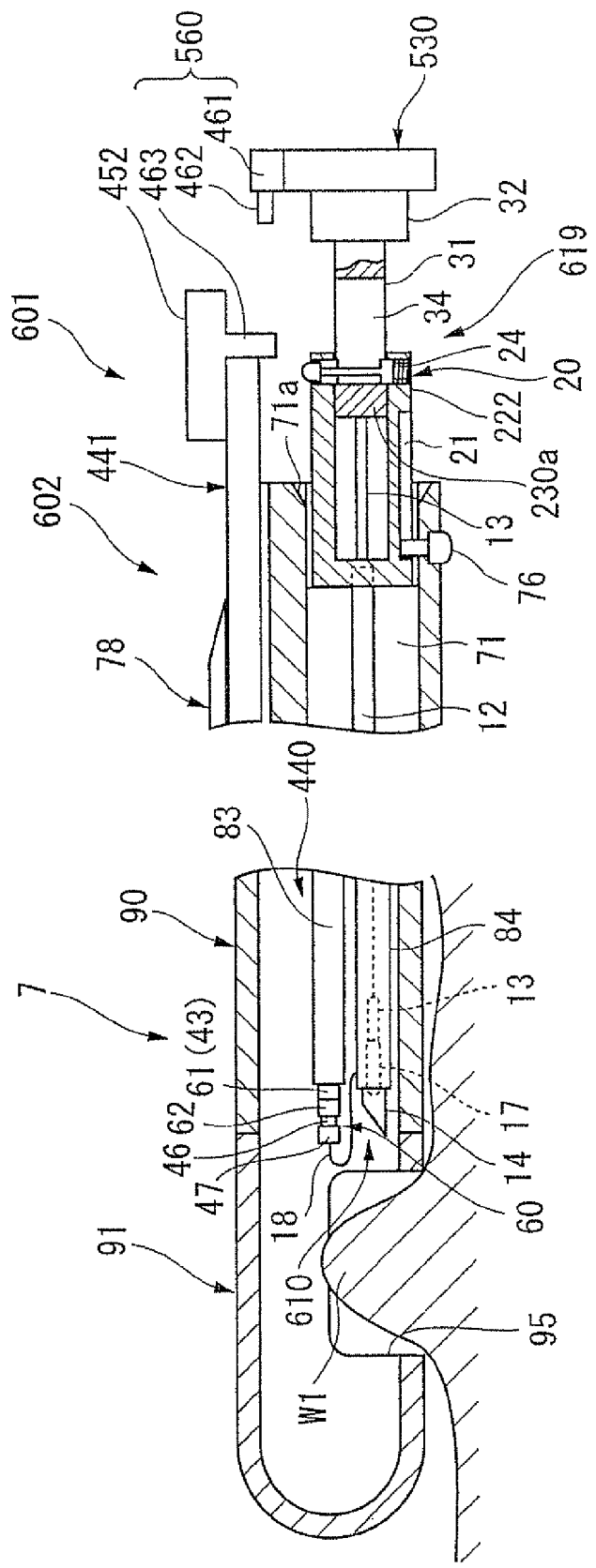
FIG. 48 is a view showing a state in which only the ligature tool is moved forward.
Figure 49:
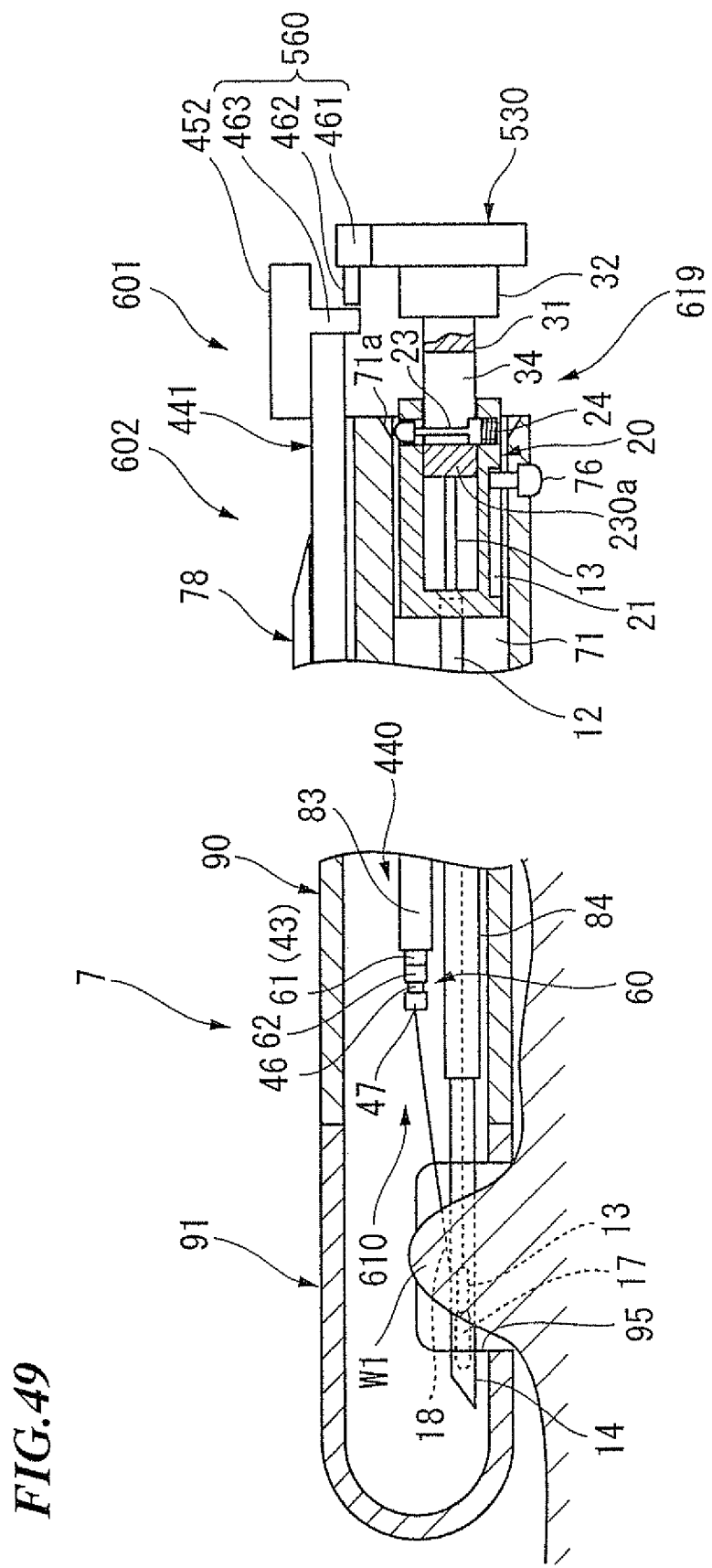
FIG. 49 is a view showing a state in which only the needle bodies are moved forward.
Figure 50:
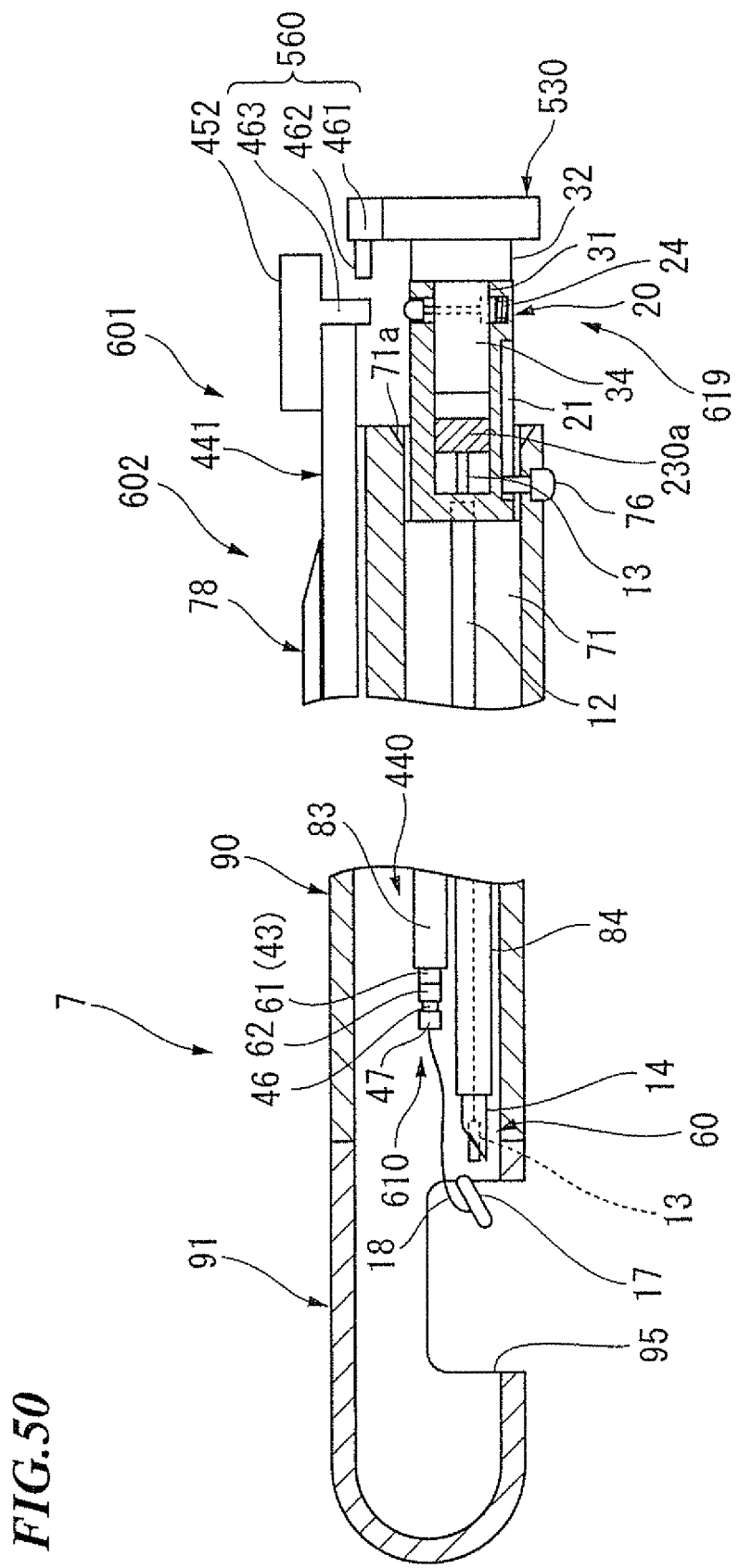
FIG. 50 is a view showing a state in which only the pushers are moved forward.

Here, as shown in FIG. 48 through FIG. 50, in the ligature and suture device for medical application 601, at least one of the puncture handle 20, the pressing handle 530, and the ligature tool 440 can be moved independently backwards or forwards.

Namely, in FIG. 48, only the ligature tool 440 is moved independently forward, and the stopper 47 is moved beforehand towards the side aperture 95.

In FIG. 49, in a state in which the linking device 560 is not operated, the puncture handle 20 is moved forward and only the needle bodies 14 are moved forward.

In FIG. 50, in a state in which the linking device 560 is not operated, only the pressing handle 530 is moved forward, and only the pushers 13 are moved forward so that the holding members 17 are discharged from the needle bodies 14. This type of operation is performed, for example, when replacing holding members 17 or when checking an operation.

Note that the present invention is not limited to the above described embodiments and may be used in a wide variety of applications.

For example, the puncture needles 10, 210, 310, and 410 may have only one needle body 14.

Each of the ligature and suture devices for medical application 1, 201, 301, 401, 501, and 601 may also not be provided with the cutter 60. Namely, it is also possible for the stopper 47 to collide directly with the distal end of the ligature sheath 43. In this case, as shown in FIG. 51, excess ligature thread is cut using forceps 6a that have been inserted into a channel in the endoscope 6. At this time, if the ligature handle 55 is slightly pressed in and the hook 45 moved forward, then the ligature thread 18 is slackened off and can easily be cut. As shown in FIG. 52, after the ligature thread 18 has been cut, then after the forceps 6a (see FIG. 49) have been housed inside the endoscope 6, the suctioning of the biomedical tissue W1 is stopped, and the overtube 7 is pulled out.

Moreover, in each of the ligature and suture devices for medical application 1, 201, 301, 401, 501, and 601, it is also possible for the respective ligature tools 40 and 440 to be ligature tools that are provided with the cutter 60.

Figure 53:
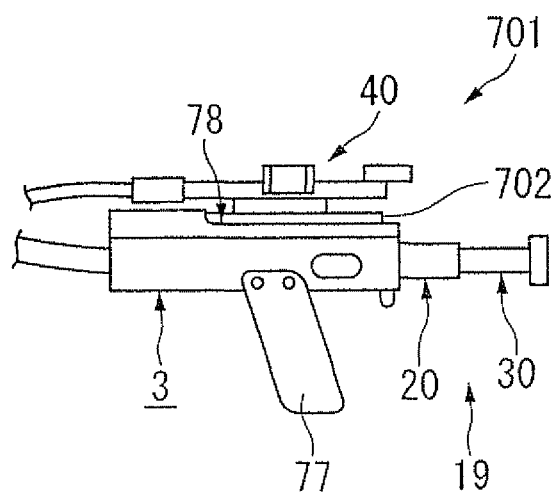
FIG. 53 is a side view showing the structure of an operation section.

In a ligature and suture device for medical application 701 such as that shown in FIG. 53, a slide member 702 is inserted in the slide receiving portion 78 so as be able to slide freely therein, and the ligature tool 40 is fixed to a top portion of the slide member 702. In this ligature and suture device for medical application 701, apart from the ligature tool 40 being on a separate axis, the remainder of the structure is the same as the ligature and suture device for medical application 701 shown in FIG. 1.

Figure 54:
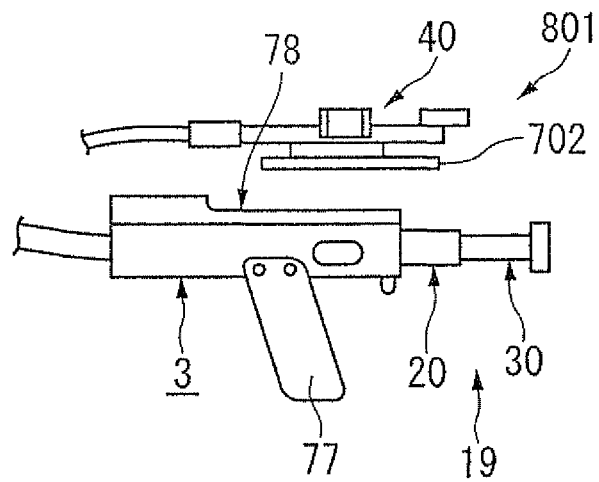
FIG. 54 is a side view showing the structure of an operation section.

Moreover, as is the case with the ligature and suture device for medical application 801 shown in FIG. 54, it is also possible to employ a structure in which the slide member 702 can be freely attached to and removed from the housing 3. In this type of ligature and suture device for medical application 801 replacing the ligature tool 40 is simple. The remainder of the structure is the same as that of the ligature and suture device for medical application 701.

Figure 55:
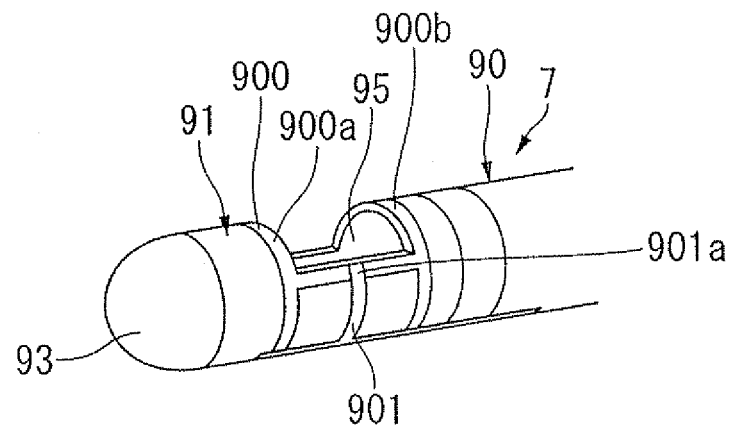
FIG. 55 is a perspective view of a distal end portion of an overtube.
Figure 56:
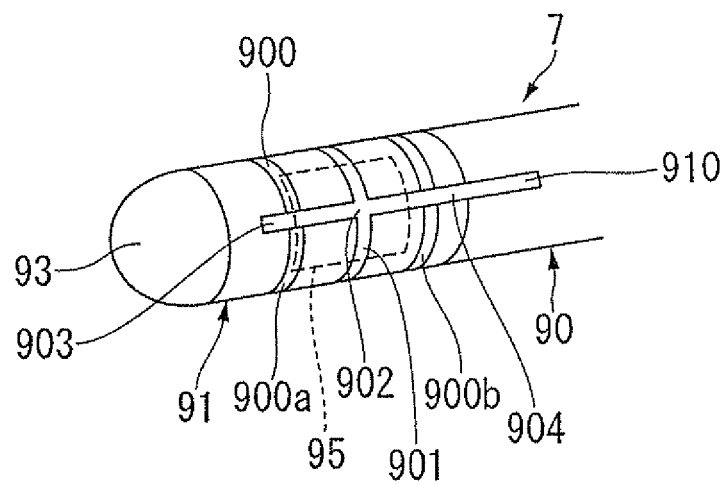
FIG. 56 is a perspective view of the distal end portion of the overtube, and shows the state shown in FIG. 50 rotated 180 degrees.
Figure 57:
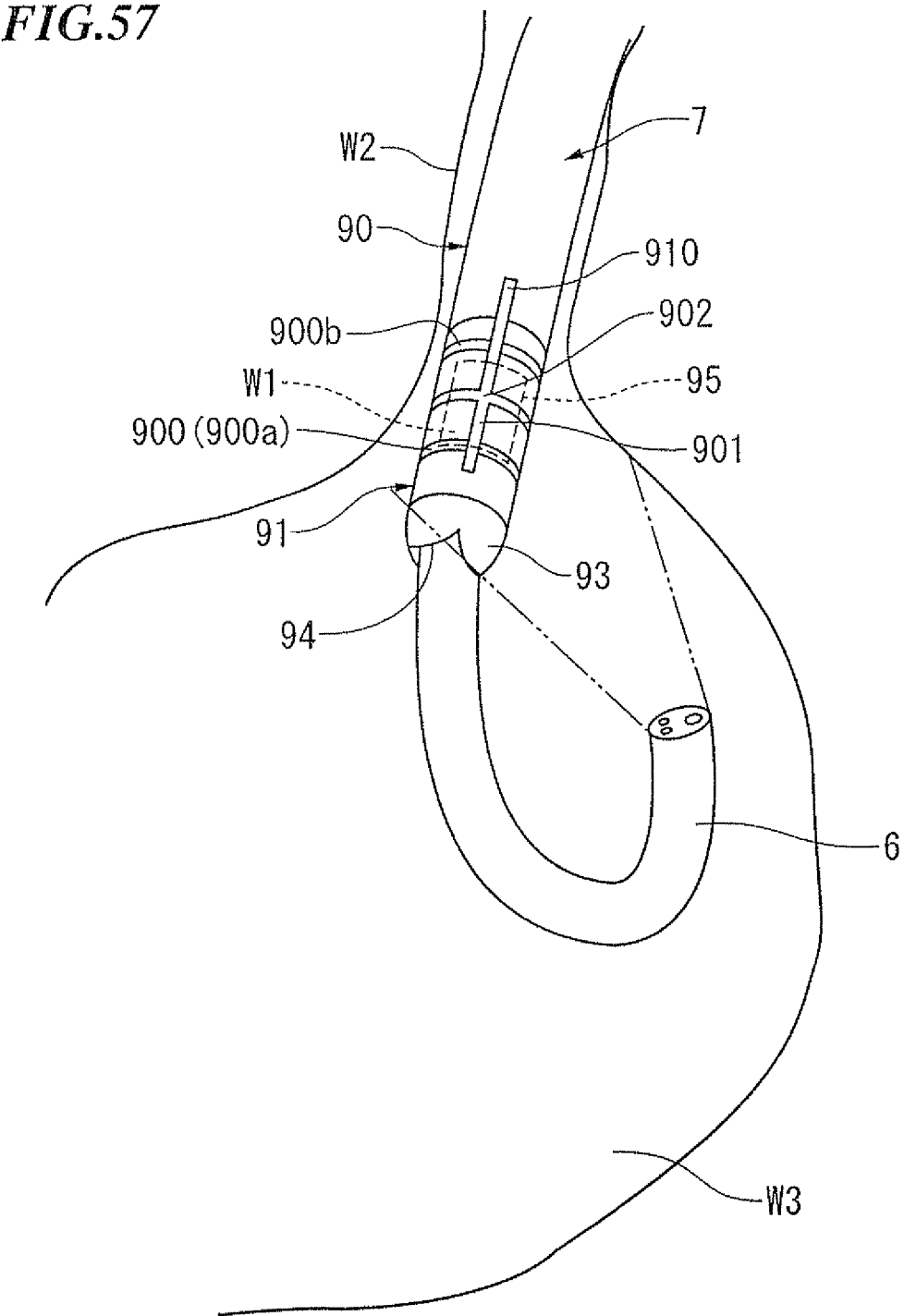
FIG. 57 is a view showing a positioning operation of a ligature and suture device for medical application.

Moreover, it is also possible to manufacture an overtube 7 such as that shown in FIG. 1 from a colorless material so as to provide a mark on the outer circumferential surface thereof that enables the positions of the biomedical tissue W1 being ligatured and of the side aperture 95 to be verified. For example, a mark 900 shown in FIG. 55 is provided on an outer circumferential surface of the distal end tube 91, running along the peripheral edge portion of the side aperture 95. In addition, inside the peripheral edge portions, toroidal portions 900a and 900b are provided extending in the circumferential direction respectively at the edge portion on the distal end side and the edge portion on the base end side. The mark 900 may be colored green, for example, in order to make it easy to distinguish it from surrounding tissue. Furthermore, as shown in FIG. 56, a cruciform mark 901 whose cross is formed running in the longitudinal direction and the circumferential direction of the distal end tube 91 is provided at a position whose phase is shifted 180 degrees from the side aperture 95. A portion 902 where the cross intersects in the mark 901 is a position whose phase is shifted 180 degrees relative to the center of the side aperture 95. As shown in FIG. 53, an end portion 901a of the portion that extends in the circumferential direction extends to the peripheral edge portion of the side aperture 95. In addition, as shown in FIG. 56, a distal end 903 and a base end of 904 of the portion that extends in the longitudinal direction extend respectively beyond the toroidal portion 900a and the toroidal portion 900b of the mark 900. This type of mark 901 may, for example, be colored blue. As shown in FIG. 57, the marks 900 and 901 are used in order to confirm the positions of the side aperture 95 and the biomedical tissue W1 using the endoscope 6 inside the body cavity. Namely, the overtube 7 is inserted via the esophagus W2 to a top portion of a stomach W3 and the endoscope 6 is made to protrude from the distal end thereof. The endoscope 6 is then bent such that the marks 900 and 901 appear in the field of vision shown virtually in the drawing. By observing the positions of the portions 900a and 900b of the mark 900, the positions of the biomedical tissue W1 and the side aperture 95 can be adjusted in the forwards and backwards direction of the overtube 7, and the position in the rotation direction of the side aperture 95 can be adjusted by observing the position of the intersection portion 902 of the mark 901.

Here, as shown in FIG. 56, it is possible to also provide a mark 910 on the tube main body 90 side. When the placements of the side aperture 95 and needle bodies 14 are at positions suitable for ligaturing, the mark 910 is provided at a position that is aligned in a straight line with the other end 904 of the mark 901. Namely, if the distal end tube 91 such as that shown in FIG. 27 and the like is able to be rotated, then if the distal end tube 91 is positioned such that the mark 901 and the mark 910 are aligned rectilinearly, then the rotation position of the distal end tube 91 can be set to the optimum position.

The ligature and suture device for medical application according to the present invention is used to ligature biomedical tissue inside a body cavity. A needle body that houses a holding member is made to penetrate biomedical tissue from one side portion thereof to the other side portion thereof and the holding member is pushed out to the other side portion side. A ligature member is attached to the holding member, and when the needle body is withdrawn from the biomedical tissue this ligature member is left penetrating the interior of the biomedical tissue from one side portion thereof to the other side portion thereof. Furthermore, a stopper is provided on one side portion side of the ligature member. As a result, if the ligaturing is conducted such that the biomedical tissue is sandwiched by the stopper and the holding member, this portion can be made to bulge out.

At this time, because the puncture handle that moves the needle body backwards and forwards, the pressing handle that moves the pressing member, which pushes out the holding member, backwards and forwards, and the ligature tool operation unit and ligature handle that are operated when ligaturing is being performed are provided so as to be able to move freely backwards and forwards inside the housing, it is possible for a procedure from the puncturing by a puncture needle to the ligaturing to be performed by an operation on the operator side.

In the above ligature and suture device for medical application, the operation section may have a linking device that links the puncture handle with the pressing handle.

In this ligature and suture device for medical application, when the pressing handle is driven, because the puncture handle is also moved in conjunction with the pressing handle due to the linking device, it is possible to move the pressing member in conjunction with the needle body. Note that when the puncture handle is driven, it is also possible for the pressing handle to be moved in conjunction with the puncture handle.

In the above ligature and suture device for medical application, the operation section may have a linking device that links the ligature tool operation unit with the pressing handle.

In this ligature and suture device for medical application, when the pressing handle is driven, because the ligature tool operation unit is also moved in conjunction with the pressing handle due to the linking device, it is possible to move the pressing member in conjunction with the stopper. As a result, is possible to prevent tensile force from acting on the ligature member. Note that when the ligature tool operation unit is driven, it is also possible for the pressing handle to be moved in conjunction with the ligature tool operation unit.

In the above ligature and suture device for medical application, the operation section may have a linking device that links the ligature tool operation unit with the puncture handle.

In this ligature and suture device for medical application, when the puncture handle is driven, because the ligature tool operation unit is also moved in conjunction with the puncture handle due to the linking device, it is possible to move the needle body in conjunction with the stopper. Note that when the ligature tool operation unit is driven, it is also possible for the puncture handle to be moved in conjunction with the ligature tool operation unit.

In the above ligature and suture device for medical application, the operation section may have a linking device that links the puncture handle with the pressing handle and the ligature tool operation unit.

This ligature and suture device for medical application has a linking device, and when the puncture handle is driven, the pressing handle and the ligature tool operation unit are moved in conjunction with the puncture handle. As a result, the pressing member and the stopper are moved in conjunction with the movement of the needle body. Note that, it is also possible for the puncture handle and the ligature tool operation unit to be moved in conjunction with the driving of the pressing handle, and it is also possible for the puncture handle and the pressing handle to be moved in conjunction with the driving of the ligature tool operation unit.

According to another ligature and suture device for medical application of the present invention, because the puncture handle is moved in conjunction with the pressing handle during the time that the puncture handle is moved from a first position to a second position and the biomedical tissue is penetrated by the needle body, it is possible to move the needle body and the pressing member forward together. Furthermore, the pressing handle and the ligature tool operation unit are moved together during the time that the puncture handle is moving to the second position. As a result, for example, by operating the pressing handle, it is possible to indirectly operate the puncture handle and the ligature tool operation unit. Namely, simply by conducting an operation in one location, it is possible to operate the ligature and suture device for medical application, and, moreover, the positions of each portion can be controlled appropriately to match the stage of treatment.

In the above ligature and suture device for medical application, the second linking device may push the pressing handle forward beyond the tissue puncture state, and the ligature tool operation unit may be moved forward interconnectedly with the pressing handle until the holding member is pushed out from the needle body.

In this ligature and suture device for medical application, when the holding member is pushed out from the needle body, the ligature tool operation unit moves forward in conjunction with the pressing member and the stopper also moves forward.

In the above ligature and suture device for medical application, the second linking device may be a device that moves the pressing handle and the ligature tool operation unit forwards and backwards independently relative to the direction in which the pressing handle moves backwards.

In this ligature and suture device for medical application, a structure is employed in which, when the pressing handle is moved backwards, the ligature tool operation unit does not move backwards in conjunction with the pressing handle.

The ligaturing and suturing method for medical application of the present invention is a method of ligaturing biomedical tissue inside a body cavity. By causing a needle body housing a holding member to penetrate the biomedical tissue from a base end side thereof to a distal end side thereof, after the holding member has been left behind at the distal end side and the needle body has been removed, the biomedical tissue is ligatured by sandwiching the biomedical tissue between the stopper on the base end side and the holding member, and this portion can be made to bulge out.

In the above ligature and suture method for medical application, there may be provided a step in which, after the needle body has punctured the biomedical tissue, the stopper is moved forward in conjunction with the forward movement of the pressing member.

In this ligaturing and suturing method for medical application, by moving the pressing member forward in conjunction with the stopper, it is possible to prevent excess tensile force from acting on the ligature member between the holding member and the stopper.

In the above ligature and suture method for medical application, there may be provided a step in which, when the needle body is being removed from the biomedical tissue, the needle body is moved backward in conjunction with the backward movement of the pressing member.

In this ligaturing and suturing method for medical application, by moving the needle body backwards in conjunction with the backward movement of the pressing member, it is possible to prevent the pressing member from being left behind inside the biomedical tissue.

In the above ligature and suture method for medical application, when the needle body is being removed from the biomedical tissue, the needle body may be moved backwards independently from the stopper.

In this ligaturing and suturing method for medical application, a structure is employed in which, when the needle body and the pressing member are moved backwards in conjunction with each other, the stopper does not move backwards in conjunction with the needle body and the pressing member. As a result, ligaturing after the needle body has been removed is simplified.

According to the present invention, when ligaturing is performed by causing a ligature member to penetrate biomedical tissue, because the device used for the ligaturing is operated by an operation section, treatment is simplified. In addition, because the operation section is formed as a single body when in use, handling is simplified. Furthermore, if a structure is employed in which any two or more of the needle body, the pressing member, and the ligature tool operation unit are operated in conjunction, the operation in the operation section is simplified.

(Additional Item 1)

In the aforementioned ligature and suture device for medical application, in the operation section, the puncture handle and the pressing handle may be provided such that they can be freely attached to or removed from the housing.

In this ligature and suture device for medical application, by removing the puncture handle and pressing handle from the housing, replacement of the puncture needles is possible.

(Additional Item 2)

In the aforementioned ligature and suture device for medical application, in the operation section, the ligature tool may be provided such that it can be freely attached to or removed from the housing.

In this ligature and suture device for medical application, by removing the ligature tool from the housing, replacement of components associated with ligature is possible.

What is claimed is:

1. A ligature and suture device for medical application, comprising:
   an insertion portion configured to be inserted into a body and being provided with at least one side aperture formed on a side at a distal end side of the insertion portion;
   a needle body that is provided inside the insertion portion, and that houses inside itself a holding member that is attached to an end portion of a ligature member that is inserted into biomedical tissue, and in which a pressing member that presses the holding member is inserted so as to move freely backwards and forwards, and that punctures biomedical tissue that has been made to bulge into the distal end insertion portion via the side aperture;
   a ligature tool that has a flexible ligature sheath that presses a stopper that is penetrated by the ligature member towards the biomedical tissue and hold the biomedical tissue between the holding member and the stopper, and that, at a distal end of an operating wire that has been inserted into the ligature sheath so as to move freely backwards and forwards, is provided with an engaging portion that engages with the ligature member that has been inserted into the stopper; and
   an operation section that is provided at a proximal end side of the insertion portion, wherein the operation section comprises:
   a housing whose distal end is connected to a proximal end portion of the insertion portion, and configured to be held by an operator;
   a puncture handle that is provided in the housing so as to move freely backwards and forwards and that drives the needle body;
   a pressing handle that is provided in the housing so as to move freely backwards and forwards and that drives the pressing member;
   a ligature tool operation unit that is provided in the housing so as to move freely backwards and forwards and that drives the ligature sheath;
   a ligature handle that is provided in the ligature tool operation unit so as to move freely backwards and forwards and that drives the engaging portion;
   a handle guide portion being formed at a proximal side of the housing along a longitudinal direction of the housing, the handle guide portion guiding a movement of the pressing handle and the puncture handle mutually substantially in parallel and in a contacting direction; wherein
   the puncture handle, the pressing handle and the ligature tool operation unit including the ligature handle are incorporated integrally in the housing, and attached to the proximal side of the housing,
   at least two of the puncture handle, the pressing handle and the ligature tool operation unit are mutually slidable and have portions which mutually contact in the sliding direction, and
   the housing guides the at least two of the puncture handle, the pressing handle and the ligature tool operation unit in the contacting direction.

2. The ligature and suture device for medical application according to claim 1, wherein the operation section has a linking device that links the puncture handle with the pressing handle.

3. The ligature and suture device for medical application according to claim 1, wherein the operation section has a linking device that links the ligature tool operation unit with the pressing handle.

4. The ligature and suture device for medical application according to claim 1, wherein the operation section has a linking device that links the ligature tool operation unit with the puncture handle.

5. The ligature and suture device for medical application according to claim 1, wherein the operation section has a linking device that links the puncture handle with the pressing handle and the ligature tool operation unit.

6. The ligature and suture device for medical application according to claim 1, wherein the housing guides the ligature tool operation unit so that the ligature tool operation unit moves substantially parallel to each of the puncture handle and the pressing handle.

7. The ligature and suture device for medical application according to claim 1, wherein the handle guide portion is formed at the proximal side of the housing along a longitudinal direction, the handle guide portion holds the puncture handle, the pressing handle and the ligature handle freely slidably mutually substantially in parallel with respect to the housing.

* * * * *